(12) United States Patent
Kondo et al.

(10) Patent No.: US 7,673,573 B2
(45) Date of Patent: Mar. 9, 2010

(54) MANUFACTURING SYSTEM AND MANUFACTURING METHOD FOR SHEET-LIKE STRUCTURE

(75) Inventors: Hideki Kondo, Kagawa-ken (JP); Masashi Hosokawa, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 488 days.

(21) Appl. No.: 11/669,290

(22) Filed: Jan. 31, 2007

(65) Prior Publication Data

US 2007/0193486 A1    Aug. 23, 2007

(30) Foreign Application Priority Data

Feb. 1, 2006    (JP)    ............... 2006-024400

(51) Int. Cl.
*D05B 3/00* (2006.01)
*A61F 13/34* (2006.01)
*D05B 27/00* (2006.01)

(52) U.S. Cl. .................. 112/475.01; 112/475.08; 28/120; 604/385.18

(58) Field of Classification Search ........... 112/475.01, 112/475.06, 475.08, 475.17, 414, 418, 429, 112/430, 439, 470.21, 470, 33, 139, 152, 112/320, 427, 132, 133, 144, 145, 146; 289/2; 383/75; 604/14, 385.18; 28/120
See application file for complete search history.

(56) References Cited

U.S. PATENT DOCUMENTS

| | | | | |
|---|---|---|---|---|
| 1,920,822 A | * | 8/1933 | West ...................... 112/470.21 |
| 2,532,438 A | | 12/1950 | Behr | |
| 2,546,623 A | * | 3/1951 | Abler ...................... 383/75 |
| 2,777,408 A | * | 1/1957 | Beck ...................... 112/470.21 |
| 2,825,474 A | * | 3/1958 | Coley et al. .................. 414/26 |
| 3,240,176 A | * | 3/1966 | Morrison ............... 112/475.18 |
| 4,515,097 A | * | 5/1985 | Rovin ...................... 112/475.06 |
| 5,080,030 A | * | 1/1992 | Taddicken .................. 112/147 |
| 5,556,205 A | * | 9/1996 | Gallie et al. .................. 383/24 |
| 6,213,040 B1 | * | 4/2001 | Shepard ............... 112/475.17 |
| 6,585,300 B1 | * | 7/2003 | Rajala et al. ................. 289/2 |
| 6,887,226 B2 | * | 5/2005 | Cassoni et al. ......... 604/385.18 |

FOREIGN PATENT DOCUMENTS

| | | |
|---|---|---|
| JP | S62-144658 A | 6/1987 |
| JP | H05-9528 A | 2/1993 |
| JP | H05-212075 A | 8/1993 |
| JP | H07-22726 A | 4/1995 |
| JP | H08-117282 A | 5/1996 |

* cited by examiner

*Primary Examiner*—Ismael Izaguirre
(74) *Attorney, Agent, or Firm*—Brinks Hofer Gilson & Lione

(57) ABSTRACT

To provide a manufacturing system and a method for manufacturing sheet-like structures. The manufacturing system of sheet-like structures comprises a loosened portion forming apparatus which forms plural loosened portions, which are substantially U-shaped on a cord member, an arranging apparatus which inserts each of the plural loosened portions into each of the plural openings formed on a belt-like member and form plural linear portions in substantial linear form which connect each of the plural loosened portions respectively, a sewing apparatus which sews a belt-like member and each of the plural linear portions together with a thread member, and a belt-like member cutting apparatus which cuts a belt-like member in prescribed forms.

16 Claims, 13 Drawing Sheets

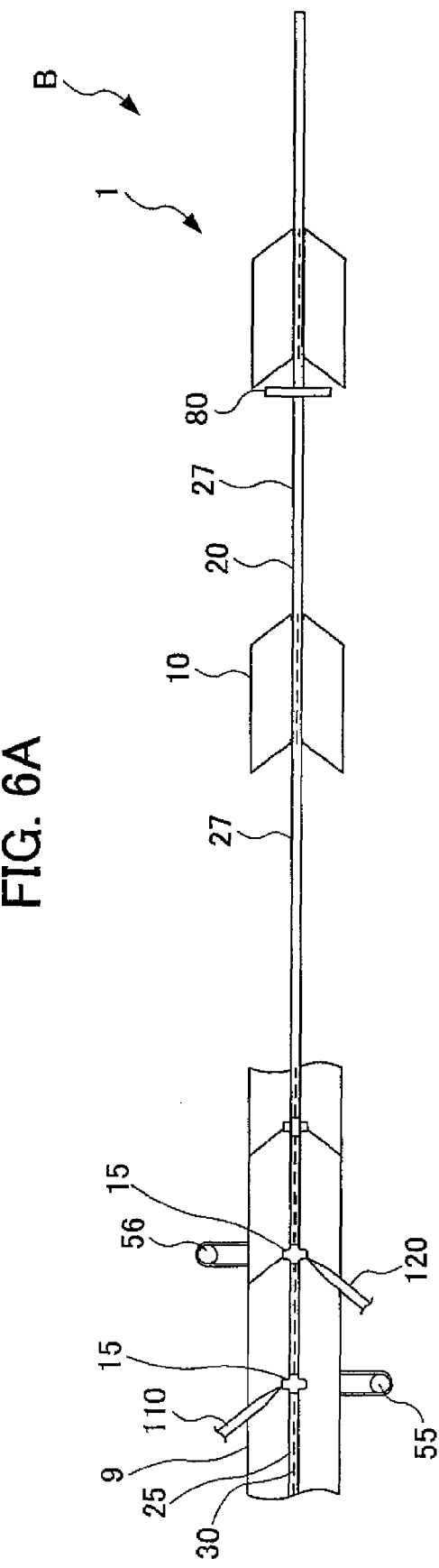
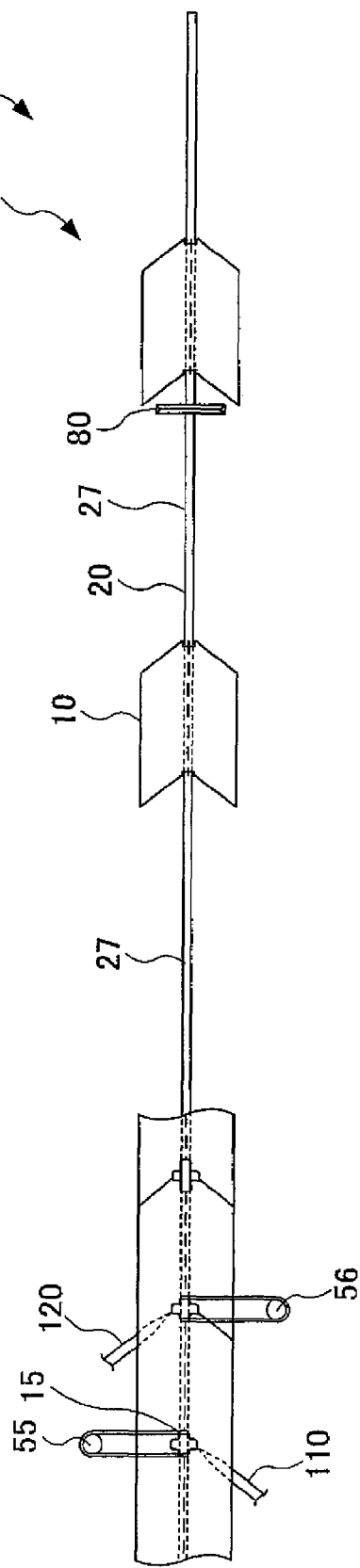

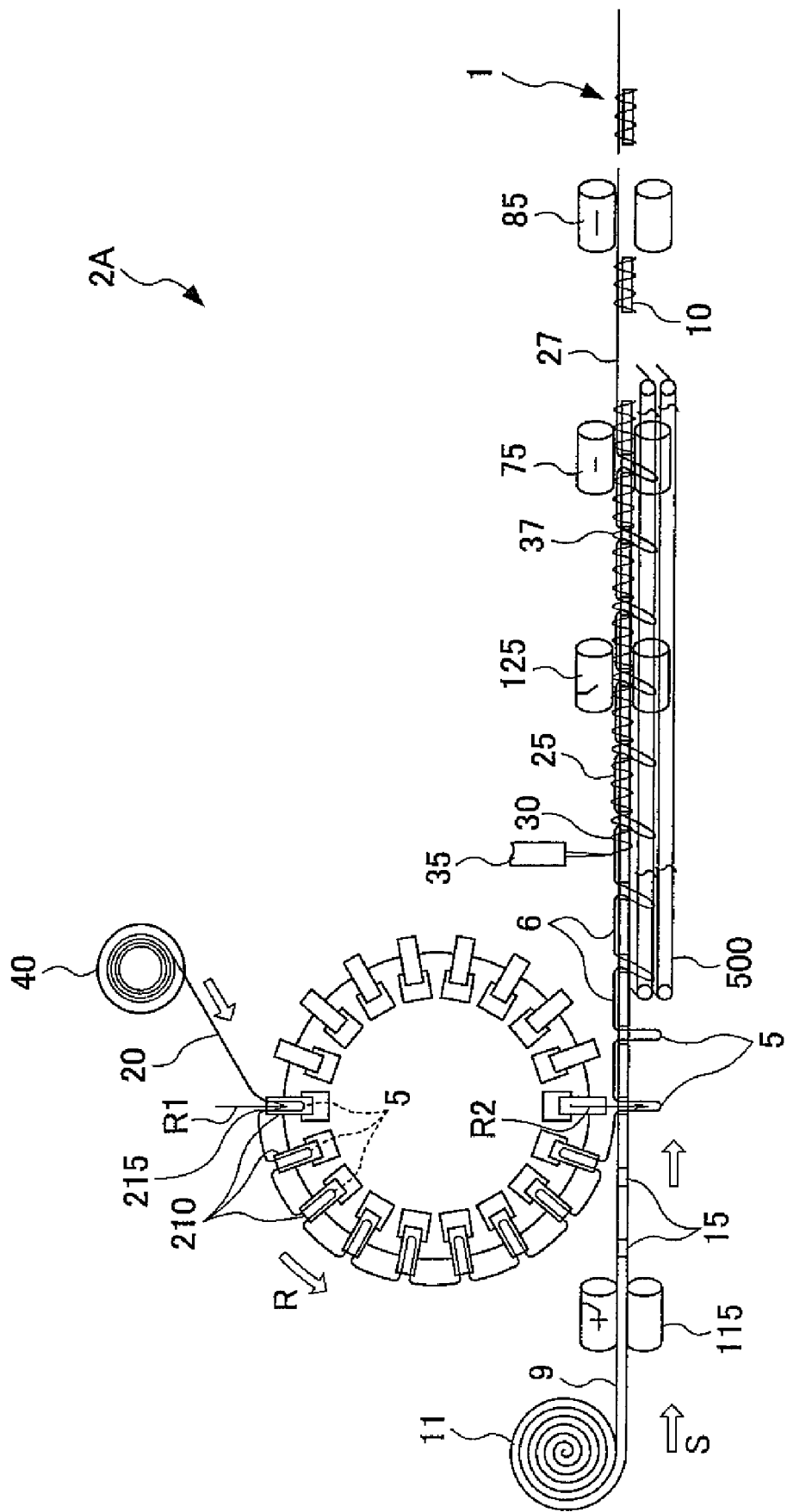

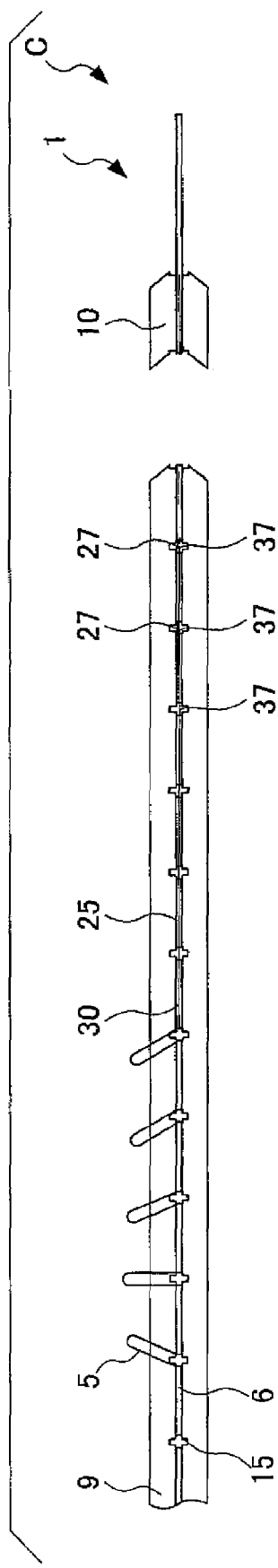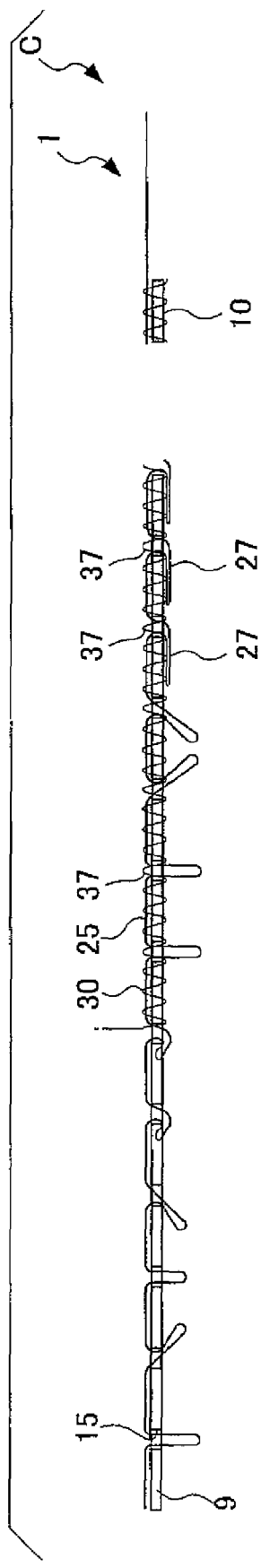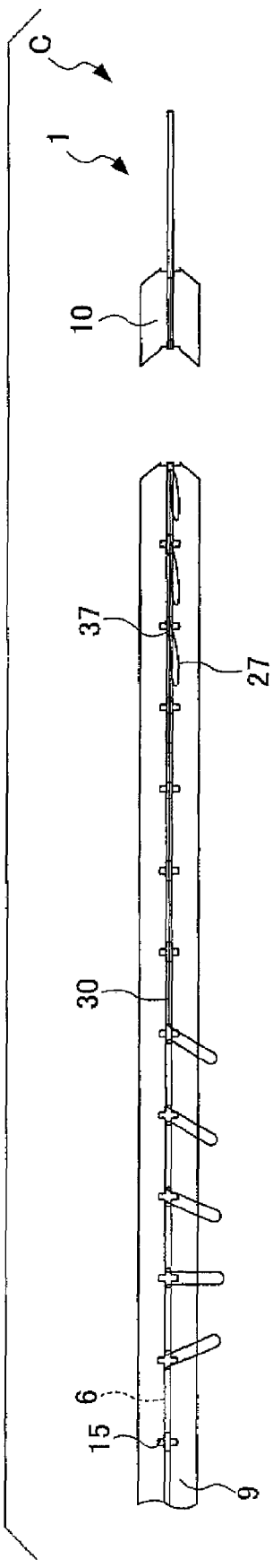
FIG. 14A
FIG. 14B
FIG. 14C

MANUFACTURING SYSTEM AND MANUFACTURING METHOD FOR SHEET-LIKE STRUCTURE

This application is based on and claims the benefit of priority from Japanese Patent Application No. 2006-024400, filed on Feb. 1, 2006, the content of which is incorporated herein by reference.

BACKGROUND OF THE INVENTION

1. Field of the Invention

The present invention relates to manufacturing systems and methods for manufacturing sheet-like structures comprising sheet members with prescribed forms and predefined cord members.

2. Related Art

Conventionally, in sewing sheet-like structures in which predefined cord members are sewn onto sheet members of a prescribed form, cord members and the sheet members are sewn together in a longitudinal direction of the cord members in order to sew the cord members and sheet members firmly. When a large quantity of sheet-like structures are manufactured continuously for example, a cord member is reeled out linearly and sewn continuously with a thread while plural sheet members are arranged at predetermined intervals so as to be in contact with the cord member. The cord member placed so as to connect each sheet member is cut to obtain prescribed sheet-like structures. In this case, a sewn area which continued from the area sewn with the sheet members is formed on the cord member with a thread member. This has caused problems in that, for example, the thread member starts to come off from free ends of the cord member in the sheet-like structures causing the thread member sewn onto the sheet member to also come off.

In order to solve the above problems, an absorbing member for tampons, which is sewn from the tail end that is a free end of the cord member toward the leading end that is the sheet-like absorbing member, with a double chain stitch for preventing the threads from coming off and for preventing separation between cord members and sheet members caused by the coming off of the threads, is disclosed in Japanese Registered Utility Model No. 2534839 (referred to as "Patent Document 1" below).

In the absorbing member stated in Patent Document 1, sewing starts from a free end of the cord member that is the tail end of the cord member toward the absorbing member that is the leading end is performed with a double chain stitch, thereby the thread is prevented from coming off by using a characteristic of the double chain stitch. That is, the double chain stitch has a characteristic in which when the seam at the tail end comes undone and only a bobbin thread is pulled off from the sewing end, the bobbin thread may come off and the whole seam may come undone; however, when the bobbin thread is pulled off from the threshold, the whole seam does not come undone. The whole thread members can be protected from coming undone as a result of the thread coming off from the free end of the extended portion that is the tail end of the absorbing member stated in Patent Document 1 by using the above characteristic of the double chain stitch.

However, the above thread coming off cannot be prevented completely in the absorbing member of Patent Document 1 because the thread member runs from the sheet member to the cord member continuously. Also, when this is used as an absorbing member for tampons, menstrual blood may leak from the free end side of the extended portion through the thread. In addition, the sewn area is formed continuously from the leading end of the absorbing member to the tail end that is a free end of the extended portion of the cord member, in the manufacturing process. Consequently, this still offer problems in that the thread is used more than necessary and the step of sewing requires excessive time. These are problems to be solved by the present invention.

SUMMARY OF THE INVENTION

In view of the abovementioned problems, an object of the present invention is to provide a manufacturing system and a method for manufacturing sheet-like structures comprising a sheet member with a prescribed form, and a cord member which is sewn onto a predefined surface of the sheet member with a specified thread member, which has an extended portion extending from an outer edge of the predefined surface, and on which a non-sewn area, without the specified thread member, is formed.

The present inventors have found a manufacturing system and a method for manufacturing that is suitable for sheet-like structures comprising a sheet member with a prescribed form and a cord member which is sewn onto a predefined surface of the sheet member with a specified thread member, which has an extended portion extending from an outer edge of the predefined surface, and on which a non-sewn area, not including the specified thread member, is formed.

A first aspect of the present invention provides a manufacturing system for a sheet-like structure, comprising: a sheet member with a prescribed form; and a cord member sewn onto a predefined surface of the sheet member with a specified thread member, having an extended portion extending from an outer edge of the predefined surface, and on which a non-sewn area, without the specified thread member, is formed; the system comprising: a loosened portion forming apparatus to form plural loosened portions which are substantially U-shaped on a cord member; an inserting portion forming apparatus to form plural cut portions or openings through which the loosened portions can be inserted on the belt-like member with an substantially belt form; an arranging apparatus to insert each of the plural loosened portions from a predefined surface of the belt-like member into each of the plural cut portions or each of the plural openings on an opposite surface of the predefined surface of the belt-like member, and to form plural linear portions formed substantially linearly on a predefined surface to connect each of the plural loosened portions respectively; a sewing apparatus to sew each of the plural linear portions arranged by the arranging apparatus and a belt-like member together using a thread member, a belt-like member cutting apparatus to form plural sheet members by cutting the belt-like member in a prescribed form so that the specified linear portion of the plural linear portions sewn by the sewing apparatus and the linear portions which lie adjacent to the specified linear portion are arranged on the different sheet members; a thread member cutting apparatus to cut thread member connecting portions which are parts of the thread member formed to connect a specified linear portion of the plural linear portions sewn by the sewing apparatus and other linear portions which lie adjacent to the specified linear portion; and a cord member cutting apparatus to cut cord connecting portions, which are parts of the cord member formed to connect a specified linear portion of the plural linear portions sewn by the sewing apparatus and other linear portions which lie adjacent to the specified linear portion at a predetermined position.

According to the first aspect of the present invention, a manufacturing system for a sheet-like structure comprising: a sheet member with a prescribed form; and a cord member sewn onto a predefined surface of the sheet member with a specified thread member having an extended portion extending from an outer edge of the predefined surface and on which a non-sewn area without the specified thread member is formed; comprises: a loosened portion forming apparatus to form plural loosened portions which are substantially U-shaped on a cord member; an inserting portion forming apparatus to form plural cut portions or openings through which the loosened portions can be inserted on the belt-like member with an substantially belt form; an arranging apparatus to insert each of the plural loosened portions from a predefined surface of the belt-like member into each of the plural cut portions or each of the plural openings on an opposite surface of the predefined surface of the belt-like member, and to form plural linear portions formed substantially linearly on a predefined surface to connect each of the plural loosened portions respectively; a sewing apparatus to sew each of the plural linear portions arranged by the arranging apparatus and a belt-like member together using a thread member, a belt-like member cutting apparatus to form plural sheet members by cutting the belt-like member in a prescribed form so that the specified linear portion of the plural linear portions sewn by the sewing apparatus and the linear portions which lie adjacent to the specified linear portion are arranged on the different sheet members; a thread member cutting apparatus to cut thread member connecting portions which are parts of the thread member formed to connect a specified linear portion of the plural linear portions sewn by the sewing apparatus and other linear portions which lie adjacent to the specified linear portion; and a cord member cutting apparatus to cut cord connecting portions, which are parts of the cord member formed to connect a specified linear portion of the plural linear portions sewn by the sewing apparatus and other linear portions which lie adjacent to the specified linear portion at a predetermined position is provided.

The manufacturing target of the manufacturing system according to the present invention is a sheet-like structure comprising a sheet member with a prescribed form, and a cord member which is sewn onto a predefined surface of the sheet member with a specified thread member, and has an extended portion extending from an outer edge of the predefined surface, on which a non-sewn area not including the specified thread member is formed. The sheet member of the sheet-like structure is a substantial sheet-like member made of a material on which cord members can be sewn with a specified thread member, and examples include fabric members, rubber members, and sheet-like absorbing members which make up the above-mentioned absorbing member for tampons. The cord member sewn onto the sheet member is acceptable as long as it is made of a material which can be sewn onto the sheet members, and examples include strings made of natural or synthesized fibers, resin-made cords, threads of more than a predetermined diameter, and composite yarns formed by twisting a number of above the above threads. Moreover, the thread member is a member that is narrowed than the predetermined diameter, and is formed of a material which can sew the sheet member and the cord member together. Examples include threads formed of natural materials, threads of synthesized fibers and fine wires.

A loosened portion forming apparatus forms plural loosened portions, which are substantially U-shaped, on a cord member reeled out from a thread supplying unit in which thread members are winded up, for example. These loosened portions become extended portions in the sheet-like structure and the linear portions described below become portions sewn onto the sheet member.

Examples of the loosened portion forming apparatus include exemplary apparatuses in the embodiments described below and suction drums arranged in a lower surface of the belt-like member which will be described later. Examples of the methods for forming loosened portions include a method in which a cord member arranged in an upper surface of the belt-like member is drawn, while a cylindrical member of a suction drum which is arranged in a lower surface of the belt-like member is inserted through an opening formed on the belt-like member. Moreover, the substantially U-shaped loosened portion can be arranged in the lower surface of the belt-like member by pulling off the cylindrical member from the opening so that the cord member (loosened portion) drawn into the cylindrical member is separated from the cylindrical member.

Examples of the loosened portion forming apparatus also include a needle-like member with its leading end having a Y-like shape and additionally including a sewing machine having a needle-like member with its leading end having Y-like shape. Examples of the methods for forming loosened portions include a method in which substantially U-shaped loosened portions are formed by inserting a cord member arranged in an upper surface of an opening formed on the belt-like member from the upper surface of the opening to the lower surface thereof by using a needle-like member with its leading end having Y-like shape. More specifically, a substantially U-shaped loosened portion can be formed and arranged in the lower surface of the belt-like member by inserting a needle-like member arranged so that its concave portion with the Y-like shape comes into contact with the cord member through the opening as it is pushing the cord member.

An inserting portion forming apparatus forms plural cut portions or openings on the belt-like member through which loosened portions can be inserted by predetermined cutters, for example. Inserting the loosened portion means cord members which form the loosened portions can be inserted.

An arranging apparatus inserts each of plural loosened portions to each of plural cut portions or plural openings from a predefined surface of the belt-like member through an opposite surface of the predefined surface of the belt-like member. An apparatus which can press loosened portions into cut portions or openings can be used. In addition, arranging apparatuses form plural linear portions formed almost linearly on a predefined surface which connects plural loosened portions, respectively. Linear portions are arranged along the surface opposite of the loosened portions inserted from the opening. The plural linear portions arranged as above are sewn onto the belt-like member continuously by means of a sewing apparatus described below.

A sewing apparatus sews each of plural sheet members arranged by an arranging apparatus and a belt-like member together with a thread member. For example, belt-like members and a cord member are sewn together by sewing along the cord member arranged on predefined surfaces of the belt-like members continuously by means of a specified sewing machine while loosened portions of the cord member are not sewn. By the above procedure, non-sewn areas can be formed on the cord members which make up the loosened portions that will be extended portions.

A belt-like member cutting apparatus forms plural sheet members by cutting the belt-like member in prescribed forms while the belt-like member is cut so that the specified linear portion of plural linear portions sewn by the sewing apparatus and the linear portion which lie adjacent to the specified linear portion are arranged on the different sheet members. Sheet members which make up the sheet-like structure are formed by the belt-like member cutting apparatus. The belt-like member is a material of the sheet members.

The belt-like member is cut at a position between a specified linear portion and linear portions which lie next to the specified linear portion to make sheet members with prescribed forms in a longitudinal direction of the belt-like member by the belt-like member cutting apparatus so that the specified linear portion sewn by the sewing apparatus and linear portions which lie adjacent to the specified linear portion are arranged on the different sheet members. The belt-like member may be cut at once or in several batches by the belt-like member cutting apparatus. The belt-like member may be cut by the belt-like member cutting apparatus before, after or at the same time as the thread-connecting portion or cord-connecting portion are cut by a thread member cutting apparatus or cord member cutting apparatus.

A thread member cutting apparatus cuts thread member-connecting portions which are parts of a thread member formed so as to connect the specified linear portion and other linear portions which lie adjacent to the specified linear portion. In addition, a cord member cutting apparatus cuts cord connecting portions, which are parts of a cord member formed so as to connect a specified linear portion of plural linear portions sewn by the sewing apparatus and other linear portions which lie adjacent to the specified linear portion at a predetermined position. As described above, cutting of the thread connecting portions by the thread member cutting apparatus or cutting of the cord connecting portions by the cord member cutting apparatus may be performed before, after or at the same time with the cutting of the belt-like member by the belt-like member cutting apparatus.

Examples of belt-like member cutting apparatus, thread member cutting apparatus or cord member cutting apparatus include specified cutter members and roll members on which a convex blade is formed on a predefined surface.

The inserting portion forming apparatus may be capable of forming each of the plural cut portions or openings in a substantial center in the width direction of the belt-like member.

According to the inserting portion forming apparatus, each of the plural cut portions or openings can be formed in a substantial center in the width direction of the belt-like member.

The loosened portions forming apparatus may form plural loosened portions by drawing in plural predetermined portions in the cord member, and the arranging apparatus pushes out each of the plural loosened portions with air and inserts each of the plural loosened portions to each of the plural cut portions or openings from a predefined surface of the belt-like member to an opposite surface of the predefined surface of the belt-like member.

According to the loosened portions forming apparatus, plural loosened portions are formed by drawing in plural predetermined portions in the cord member. The arranging apparatus pushes out each of the plural loosened portions with air and inserts each of the plural loosened portions to each of the plural cut portions or openings from a predefined surface of the belt-like member to an opposite surface of the predefined surface of the belt-like member. This allows the loosened portions to be formed and inserted by an apparatus using air pressure, for example.

The arranging apparatus may arrange the plural linear portions lined up in substantially linearly, and the sewing apparatus may sew each of the plural linear portions lined up in a substantially linear form by the arranging apparatus continuously onto the belt-like member along a straight line formed by the plural linear portions.

According to the arranging apparatus, the plural linear portions are arranged along with each other in substantially linearly. The sewing apparatus sews each of the plural linear portions lined up in a substantially linear form by the arranging apparatus continuously onto the belt-like member along a straight line formed by the plural linear portions. This enables sewing to be performed easily by a sewing apparatus and allows precise sewing to be performed continuously.

The sewing apparatus may further comprise a primary evacuating apparatus to evacuate each of the plural loosened portions to avoid overlapping the straight line formed by the plural linear portions.

According to the sewing apparatus, there is provided a primary evacuating apparatus to evacuate each of the plural loosened portions to avoid overlapping the straight line formed by the plural linear portions. This enables prevention of loosened portions from being sewn onto the sewn areas formed along a straight line formed by plural linear portions by the sewing apparatus.

The belt-like member cutting apparatus may comprise a predetermined cutting unit, and a secondary evacuating apparatus to evacuate the cord connecting portion from a cutting position at which the belt-like member is cut by the cutting unit.

According to the belt-like member cutting apparatus, there are provided a predetermined cutting unit, and a secondary evacuating apparatus to evacuate the cord connecting portion from a cutting position at which the belt-like member is cut by the cutting unit. This enables prevention of the cord connecting portions from being cut at undesired positions when cutting at predetermined positions of the belt-like member.

The thread member cutting apparatus, and the cord member cutting apparatus may be the same cutting unit, and the manufacturing system may further comprise a conveying apparatus for moving the cord connecting portion to the cutting position in the cutting unit.

According to the belt-like member cutting apparatus, the thread member cutting apparatus, and the cord member cutting apparatus are the same cutting unit, and the manufacturing system further comprises a conveying apparatus for moving the cord connecting portion to the cutting position in the cutting unit. This enables cutting a belt-like member, thread member and cord member simultaneously at a cutting position.

The belt-like member may be a belt-like absorbing member comprising a predetermined absorbing layer with liquid absorbability coated with a surface material of a thin film form, and the manufacturing system may further comprise a belt-like member forming apparatus for covering the absorbing layer with the surface material.

According to the abovementioned structure, a belt-like member is a belt-like absorbing member comprising a predetermined absorbing layer with liquid absorbability coated with a surface material of a thin film form, and the manufacturing system further comprise a belt-like member forming apparatus for covering the absorbing layer with the surface material. This allows formation of a belt-like absorbing member by applying a surface material to the fibrous absorbing layer for preventing unraveling of the fibrous absorbing layer, and enables sewing the above-mentioned cord member and the like onto the absorbing member formed into a belt-like form.

Further, the second aspect of the present invention provides a method for manufacturing a sheet-like structure, comprising a sheet member with a prescribed form, and a cord member, sewn onto a predefined surface of the sheet member with a specified thread member, and having an extended portion extending from an outer edge of the predefined surface on which a non-sewn area without the specified thread member is formed, the method comprising steps of: forming loosened portion to form plural loosened portions which are substantially U-shaped on a cord member; forming inserting portion to form plural cut portions or openings on the belt-like member with an approximate belt form through which the loosened portions can be inserted; arranging to insert each of the plural loosened portions from a predefined surface of the belt-like member into each of the plural cut portions or each of the plural openings on an opposite surface of the predefined surface of the belt-like member, and to form plural linear portions formed substantially linearly on a predefined surface to connect each of the plural loosened portions respectively; sewing to sew each of the plural linear portions arranged by the arranging apparatus and a belt-like member together using a thread member, cutting a belt-like member to form plural sheet members by cutting the belt-like member in a prescribed form so that the specified linear portion of the plural linear portions sewn by the sewing apparatus and the linear portions which lie adjacent to the specified linear portion are arranged on the different sheet members; cutting a thread member to cut thread member connecting portions which are parts of the thread member formed to connect a specified linear portion of the plural linear portions sewn by the sewing apparatus and other linear portions which lie adjacent to the specified linear portion; and cutting a cord member to cut cord connecting portions, which are parts of the cord member formed to connect a specified linear portion of the plural linear portions sewn by the sewing apparatus and other linear portions which lie adjacent to the specified linear portion at a predetermined position.

According to the second aspect of the present invention, the method for manufacturing a sheet-like structure comprises a sheet member with a prescribed form, and a cord member, sewn onto a predefined surface of the sheet member with a specified thread member, and having an extended portion extending from an outer edge of the predefined surface on which a non-sewn area without the specified thread member is formed. The method comprising steps of: forming loosened portion to form plural loosened portions which are substantially U-shaped on a cord member; forming inserting portion to form plural cut portions or openings on the belt-like member with an approximate belt form through which the loosened portions can be inserted; arranging to insert each of the plural loosened portions from a predefined surface of the belt-like member into each of the plural cut portions or each of the plural openings on an opposite surface of the predefined surface of the belt-like member, and to form plural linear portions formed substantially linearly on a predefined surface to connect each of the plural loosened portions respectively; sewing to sew each of the plural linear portions arranged by the arranging apparatus and a belt-like member together using a thread member. The method further comprises steps of cutting a belt-like member to form plural sheet members by cutting the belt-like member in a prescribed form so that the specified linear portion of the plural linear portions sewn by the sewing apparatus and the linear portions which lie adjacent to the specified linear portion are arranged on the different sheet members; cutting a thread member to cut thread member connecting portions which are parts of the thread member formed to connect a specified linear portion of the plural linear portions sewn by the sewing apparatus and other linear portions which lie adjacent to the specified linear portion; and cutting a cord member to cut cord connecting portions, which are parts of the cord member formed to connect a specified linear portion of the plural linear portions sewn by the sewing apparatus and other linear portions which lie adjacent to the specified linear portion at a predetermined position.

The manufacturing target of the method for manufacturing according to the present invention is a sheet-like structure comprising a sheet member with a prescribed form, and a cord member which is sewn onto a predefined surface of the sheet member with a specified thread member and has an extended portion extending from an outer edge of the predefined surface, on which non-sewn area is formed without the specified thread member. The sheet member of the sheet-like structure is a substantial sheet-like member made of a material on which cord members can be sewn with a specified thread member, and examples include fabric members, rubber members, and sheet-like absorbing members which make up the above-mentioned absorbing member for tampons. The cord member sewn onto the sheet member is acceptable as long as it is made of a material which can be sewn onto the sheet members, and examples include strings made of natural or synthesized fibers, resin-made cords, threads of more than a predetermined diameter and composite yarns formed by twisting a number of the above threads. Moreover, the thread member is a member that is narrower than a predetermined diameter, formed of a material which can sew the sheet member and the cord member together, and examples include threads formed of natural materials, threads of synthesized fibers and fine wires.

In a step of forming the loosened portion, plural loosened portions, which are substantially U-shaped, are formed on a cord member reeled out from a thread supplying unit in which thread members are winded up, for example. These loosened portions become extended portions in the sheet-like structure and the linear portions described below become portions sewn onto the sheet member.

Examples of the step of forming the loosened portion include exemplary steps in the embodiments described below and a method in which a cord member arranged in an upper surface of the belt-like member is drawn while a cylindrical member of the suction drum which is arranged in a lower surface of the belt-like member, is inserted through an opening formed on the belt-like member. Moreover, the substantially U-shaped loosened portion can be arranged in the lower surface of the belt-like member by pulling off the cylindrical member from the opening so as for the cord member (loosened portion) drawn into the cylindrical member is separated from the cylindrical member.

Moreover, examples of the methods for forming loosened portions include a method in which substantially U-shaped loosened portions are formed by inserting a cord member arranged in an upper surface of an opening formed on the belt-like member from the upper surface of the opening to the lower surface thereof by using a needle-like member with its leading end having Y-like shape. More specifically, a substantially U-shaped loosened portion can be formed and arranged in the lower surface of the belt-like member by inserting a needle-like member arranged so that its concave portion with the Y-like shape comes into contact with the cord member through the opening as it is pushing the cord member.

In a step of forming the inserting portion, plural cut portions or openings are formed on the belt-like member by predetermined cutters, through which loosened portions can be inserted, for example. Inserting the loosened portion means the cord members which form loosened portions can be inserted, and configurations during insertion are not limited.

In a step of arranging, each of the plural loosened portions is inserted to each of the plural cut portions or openings from a predefined surface of the belt-like member through an opposite surface of the predefined surface of the belt-like member. An apparatus which can press the loosened portions into cut portions or openings is usable. In addition, plural linear portions formed almost linearly on a predefined surface connecting the plural loosened portions respectively are formed in the step of arranging. Linear portions are arranged along the surface opposite the loosened portions inserted from the openings. The plural linear portions arranged as above can be sewn onto the belt-like member continuously in a step of sewing described below.

In the step of sewing, each of the plural sheet members arranged in the step of arranging and a belt-like member are sewn together with a thread member. For example, belt-like members and a cord member are sewn together by sewing continuously along the cord member arranged on predefined surfaces of the belt-like members by means of a specified sewing machine while loosened portions of the cord member are not sewn. In this way, non-sewn areas can be formed on the cord members which make up the loosened portions that will be extended portions.

In a step of cutting a belt-like member, plural sheet members are formed by cutting the belt-like member in prescribed forms so as for the specified linear portion of the plural linear portions sewn in the step of sewing and the linear portion which lie adjacent to the specified linear portion are arranged on the different sheet members. Sheet members which make up the sheet-like structure are formed in the step of cutting the belt-like member. The belt-like member is a material of the sheet members.

The belt-like member is cut at a position between a specified linear portion and linear portions which lie next to the specified linear portion in a longitudinal direction of the belt-like member to make sheet members with prescribed forms in the step of cutting the belt-like member so that the specified linear portion sewn in the step of sewing and linear portions which lie adjacent to the specified linear portion are arranged on the different sheet members. The belt-like member may be cut at once or in several batches in the step of cutting the belt-like member. The belt-like member may be cut in the step of cutting the belt-like member before, after or at the same time as the thread-connecting portion or cord-connecting portion are cut in a step of cutting the thread member or a step of cutting the cord member.

The thread connecting portions, which are parts of a thread member formed so as to connect the specified linear portion and other linear portions which lie adjacent to the specified linear portion, are cut in the step of cutting the thread member. In addition, cord connecting portions, which are parts of a cord member formed so as to connect a specified linear portion of the plural linear portions sewn by the sewing apparatus and other linear portions which lie adjacent to the specified linear portion, are cut at a predetermined position in the step of cutting the cord member. As described above, cutting of the thread connecting portions in the step of cutting the thread member or cutting of the cord connecting portions in the step of cutting the cord member may be performed before, after or at the same time with the cutting of the belt-like member in the step of cutting the belt-like member.

Examples of the cutting apparatuses used in the step of cutting the belt-like member, cutting the thread member, or cutting the cord member include specified cutter members and roll members with a convex blade formed on a predefined surface thereof.

The forming inserting portion step may be capable of forming each of the plural cut portions or openings in a substantial center in the width direction of the belt-like member.

According to the forming inserting portion step, each of the plural cut portions or openings can be formed in a substantial center in the width direction of the belt-like member.

The forming loosened portions step may form plural loosened portions by drawing in plural predetermined portions in the cord member, and the arranging step may push out each of the plural loosened portions with air and inserts each of the plural loosened.

According to the forming loosened portions step, the method for manufacturing a sheet-like structure forms plural loosened portions by drawing in plural predetermined portions in the cord member, and the arranging step pushes out each of the plural loosened portions with air and inserts each of the plural loosened. This allows the loosened portions to be formed and inserted by an apparatus using air pressure, for example.

The arranging step may arrange the plural linear portions lined up in substantially linearly, and the sewing step may sew each of the plural linear portions lined up in a substantially linear form by the arranging apparatus continuously onto the belt-like member along a straight line formed by the plural linear portions.

According to the arranging step, the method for manufacturing a sheet-like structure arranges the plural linear portions lined up in substantially linearly, and the sewing step sews each of the plural linear portions lined up in a substantially linear form by the arranging apparatus continuously onto the belt-like member along a straight line formed by the plural linear portions. This enables sewing in the step of sewing to be performed easily and allows precise sewing to be performed continuously.

The sewing step may further comprise a primary evacuating apparatus to evacuate each of the plural loosened portions to avoid overlapping the straight line formed by the plural linear portions.

According to the sewing step, the method for manufacturing a sheet-like structure further comprises a primary evacuating apparatus to evacuate each of the plural loosened portions to avoid overlapping the straight line formed by the plural linear portions. This enables prevention of loosened portions from being sewn onto the sewn areas formed along a straight line formed by plural linear portions in the step of sewing.

The cutting the belt-like member step may comprise a predetermined cutting unit, and a secondary evacuating apparatus to evacuate the cord connecting portion may from a cutting position at which the belt-like member is cut by the cutting unit.

According to the cutting the belt-like member step, the method for manufacturing a sheet-like structure comprises a predetermined cutting unit, and a secondary evacuating apparatus to evacuate the cord connecting portion from a cutting position at which the belt-like member is cut by the cutting unit. This enables prevention the cord connecting portions from being cut at undesired positions when cutting predetermined positions of the belt-like member.

The cutting a belt-like member step, the cutting thread member step and cutting the cord member step may be performed by the same cutting unit, and the cord connecting portion may be moved to a cutting position in the cutting unit by a predetermined conveying apparatus.

According to the aspect, in the method for manufacturing a sheet-like structure, the cutting a belt-like member step, the cutting thread member step and cutting the cord member step are performed by the same cutting unit, and the cord connecting portion is moved to a cutting position in the cutting unit by a predetermined conveying apparatus. This enables cutting belt-like member, thread member and cord member simultaneously at a cutting position.

The belt-like member may be a belt-like absorbing member comprising a predetermined absorbing layer with liquid absorbability coated with a surface material of a thin film form, and the method may further comprise a step of forming a belt-like member for covering the absorbing layer with the surface material.

According to the aspect, the belt-like member is a belt-like absorbing member comprising a predetermined absorbing layer with liquid absorbability coated with a surface material of a thin film form, and the method further comprises a step of forming a belt-like member for covering the absorbing layer with the surface material. This allows forming of a belt-like absorbing member by applying a surface material to the fibrous absorbing layer for preventing unraveling of the fibrous absorbing layer, and enables sewing the above-mentioned cord member onto the absorbing member formed into a belt-like form.

The present invention can provide a manufacturing system and a method for manufacturing sheet-like structures comprising a sheet member with a prescribed form, and a cord member which is sewn onto a predefined surface of the sheet member with a specified thread member, and has an extended portion extending from an outer edge of the predefined surface, on which a non-sewn area, without the specified thread member, is formed.

BRIEF DESCRIPTION OF THE DRAWINGS

FIG. 6A shows an enlarged view of area B in FIG. 4;

FIG. 6B shows an enlarged view of area B in FIG. 4;

FIG. 7 shows a view describing a manufacturing system of the second embodiment of the present invention;

FIG. 14A shows a view describing manufacture of sheet-like structures in the manufacturing system of the fifth embodiment;

FIG. 14B shows a view describing manufacture of sheet-like structures in the manufacturing system of the fifth embodiment;

FIG. 14C shows a view describing manufacture of sheet-like structures in the manufacturing system of the fifth embodiment.

DETAILED DESCRIPTION OF THE INVENTION

The preferred embodiments for implementing the present invention will be described referring to figures below.

Figure 1:
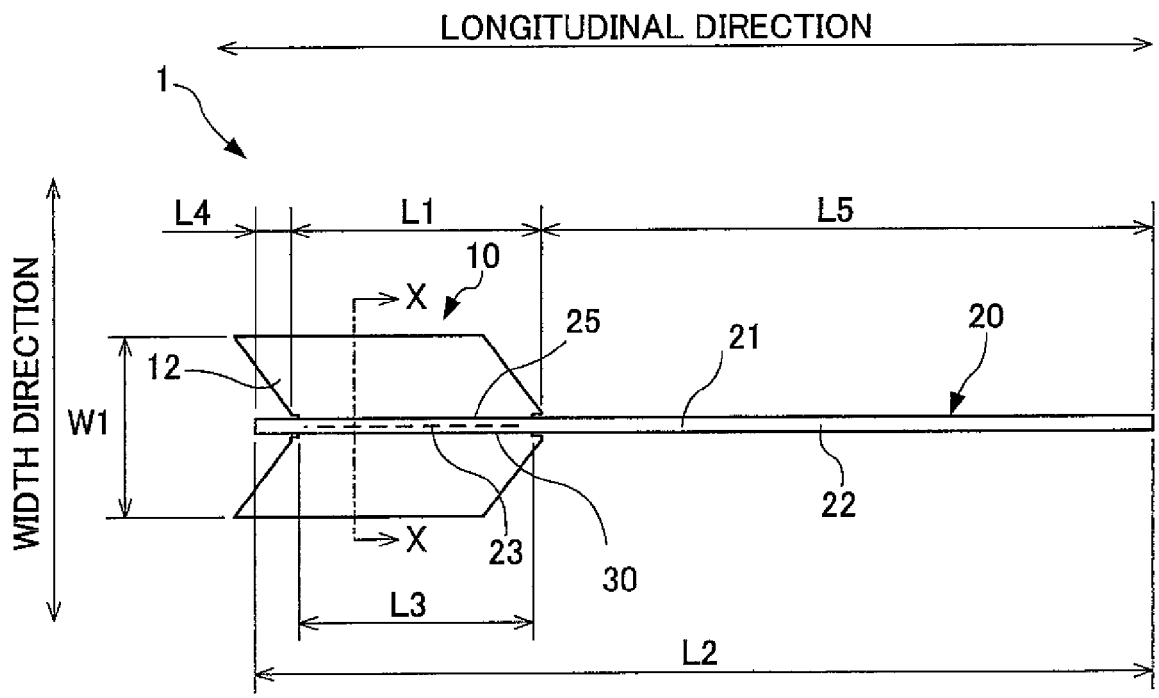
FIG. 1 shows a plan view of the sheet-like structure of Example 1.
Figure 2:
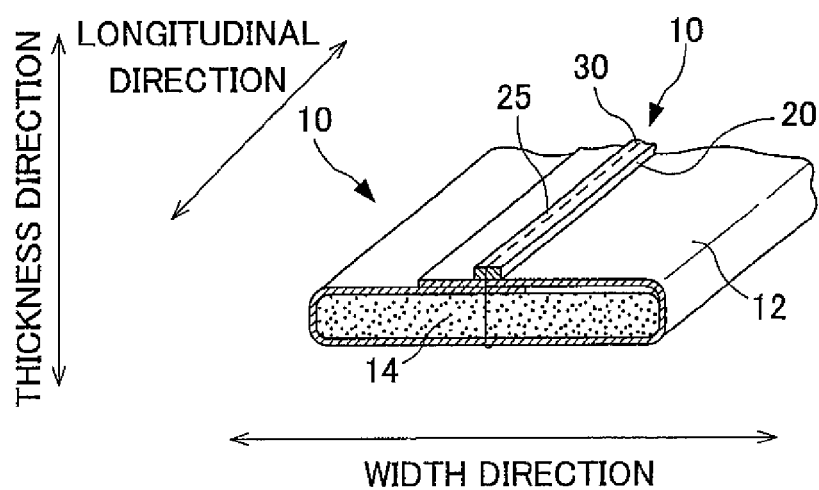
FIG. 2 shows a cross section of X-X line of FIG. 1.
Figure 3:
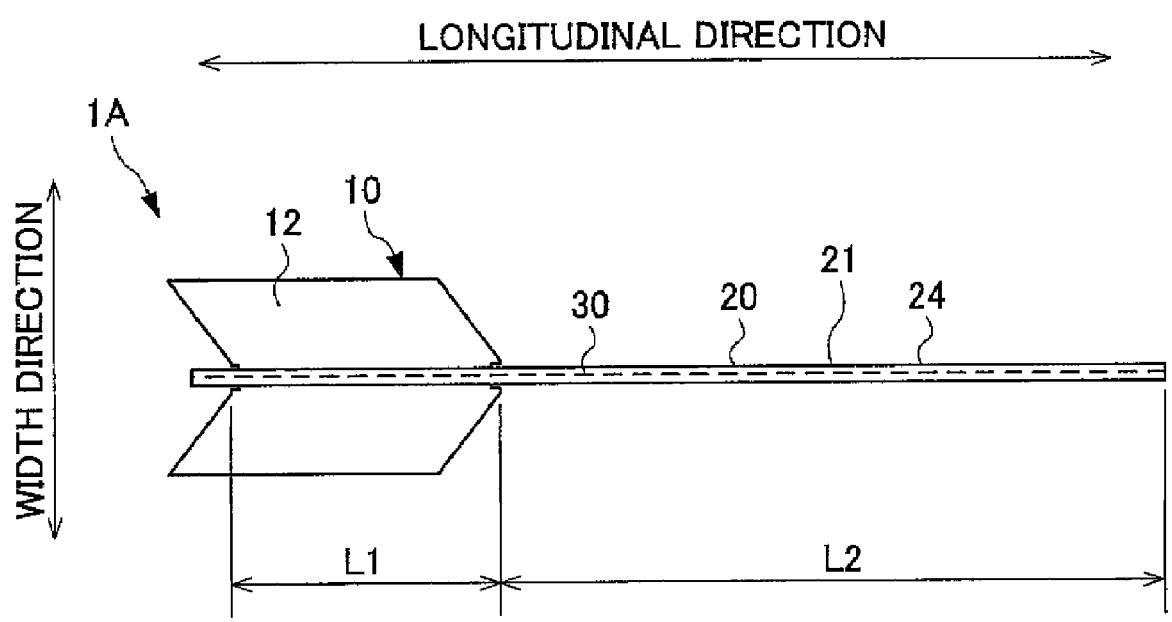
FIG. 3 shows a plan view of a conventional sheet-like structure.
Figure 4:
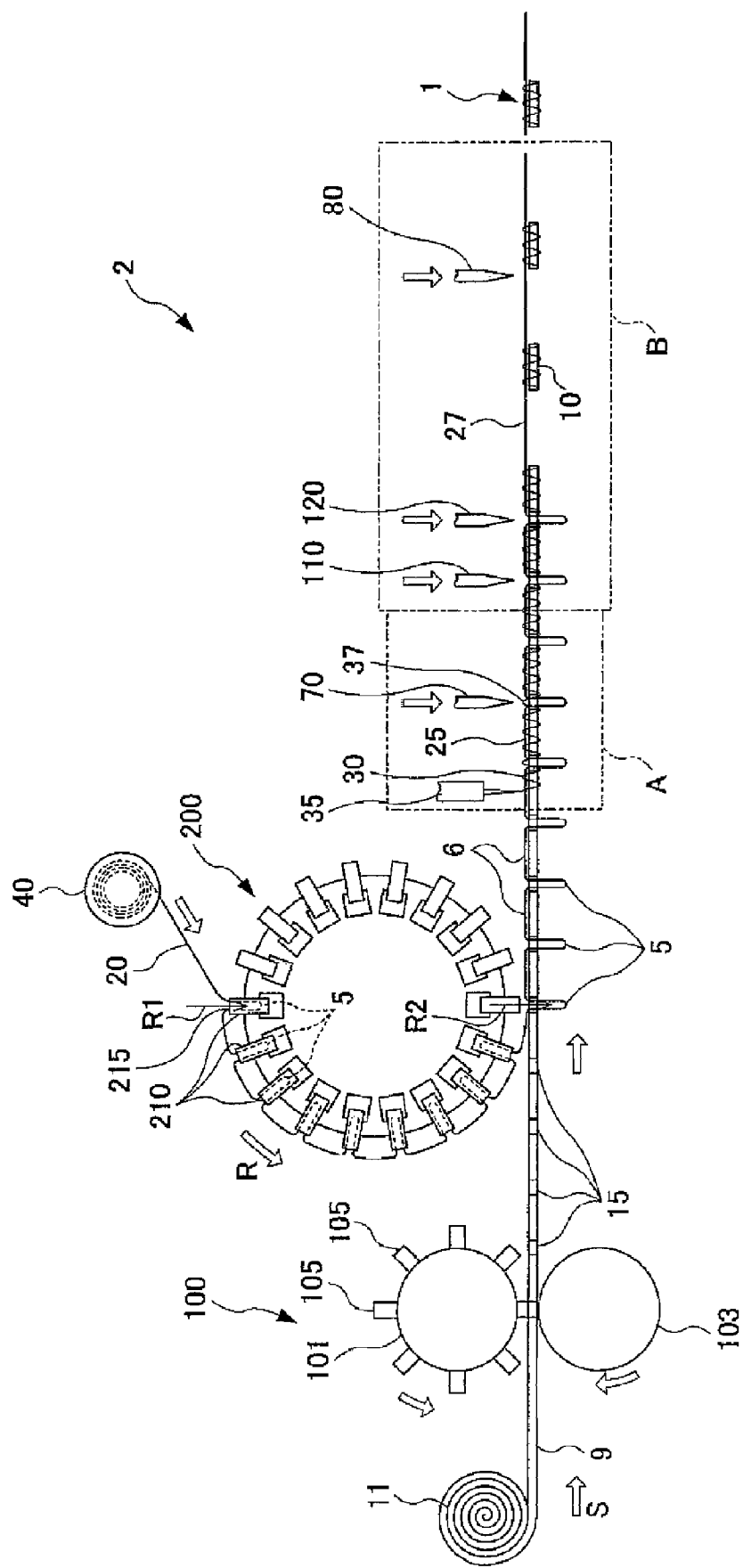
FIG. 4 shows a view describing a manufacturing system of the first embodiment of the present invention.
Figure 5A:
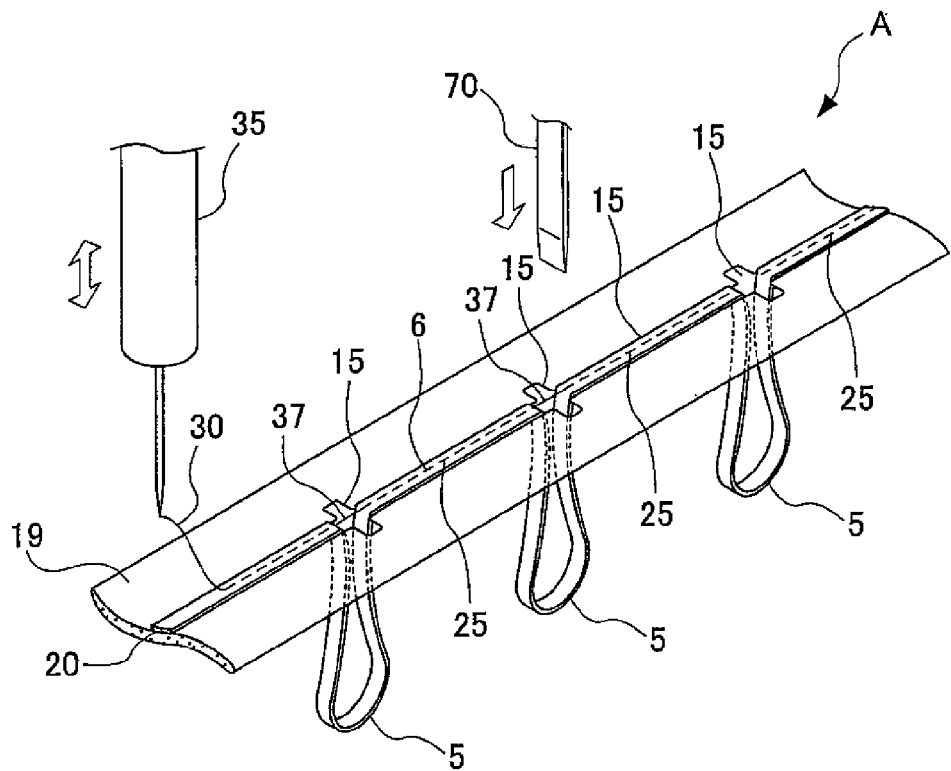
FIG. 5A shows an enlarged view of area A in FIG. 4.
Figure 5B:
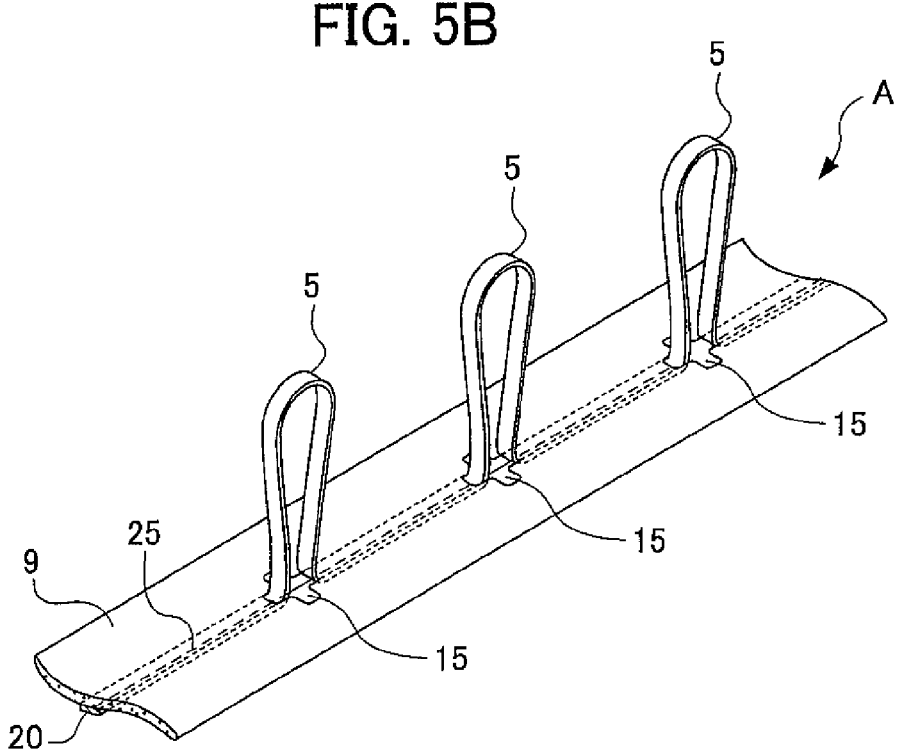
FIG. 5B shows an enlarged view of area A in FIG. 4.
Figure 8:
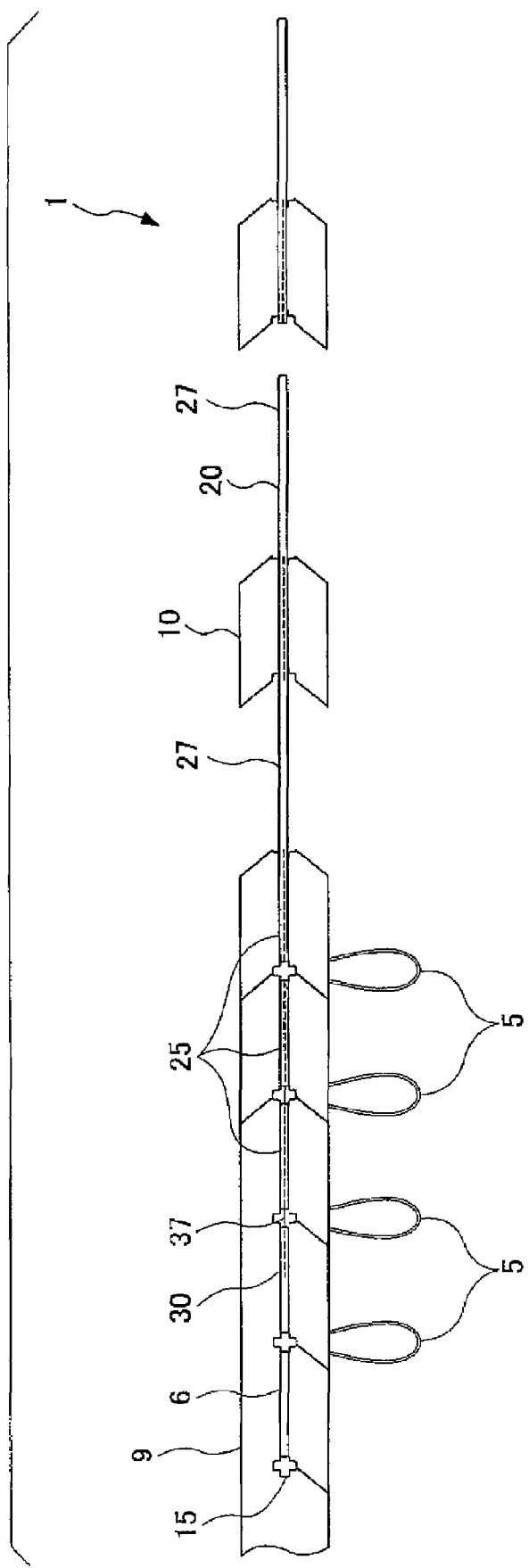
FIG. 8 shows a view describing manufacture of sheet-like structures in the manufacturing system of the second embodiment of the present invention.
Figure 9:
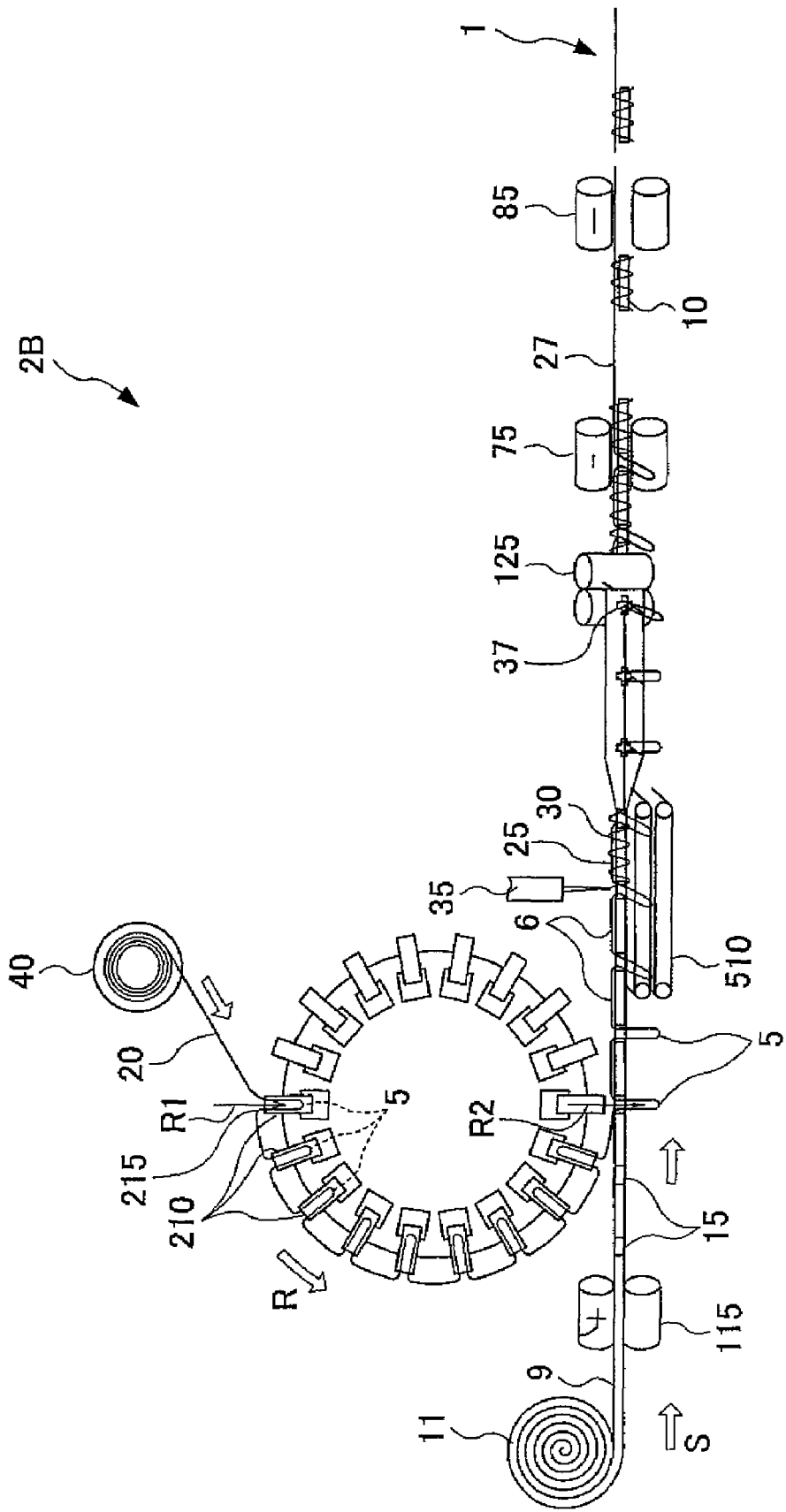
FIG. 9 shows a view describing a manufacturing system of the third embodiment of the present invention.
Figure 10:
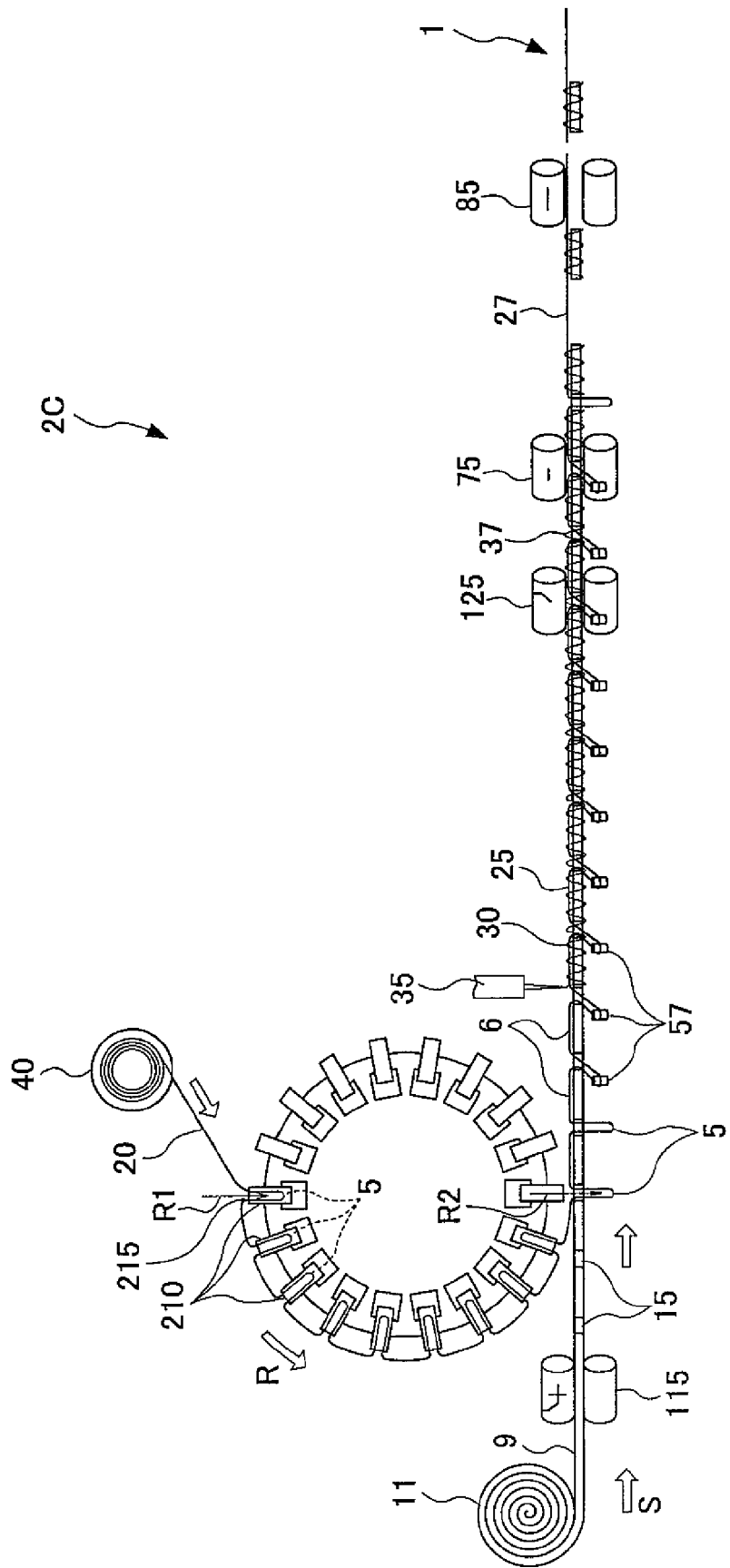
FIG. 10 shows a view describing a manufacturing system of the fourth embodiment of the present invention.
Figure 11:
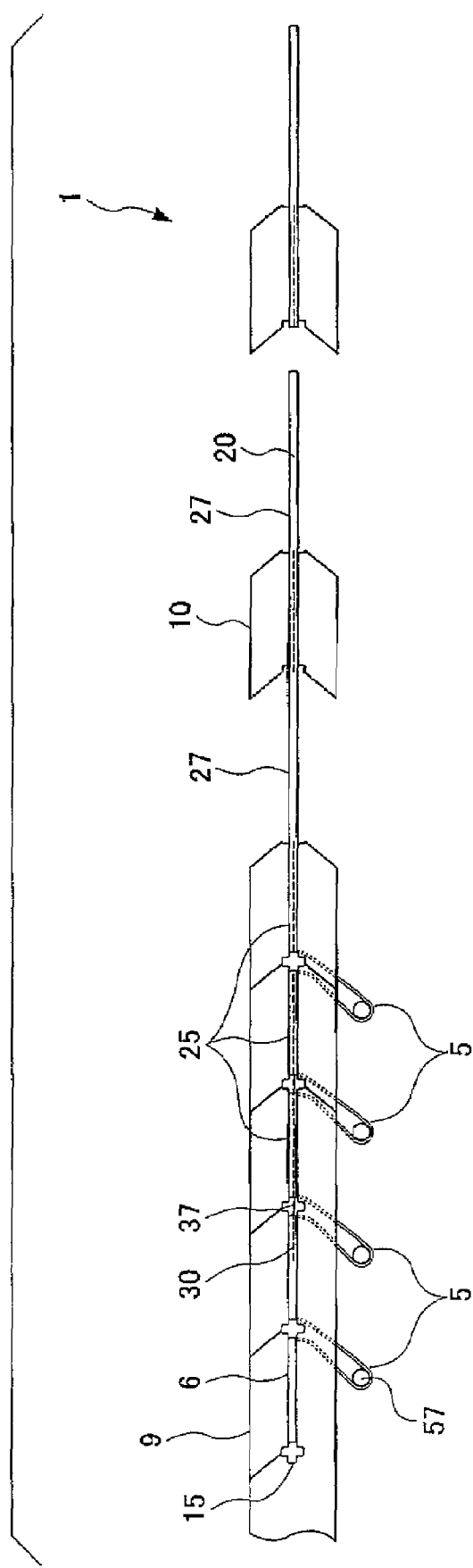
FIG. 11 shows a view describing manufacture of sheet-like structures in the manufacturing system of the fourth embodiment of the present invention.
Figure 12:
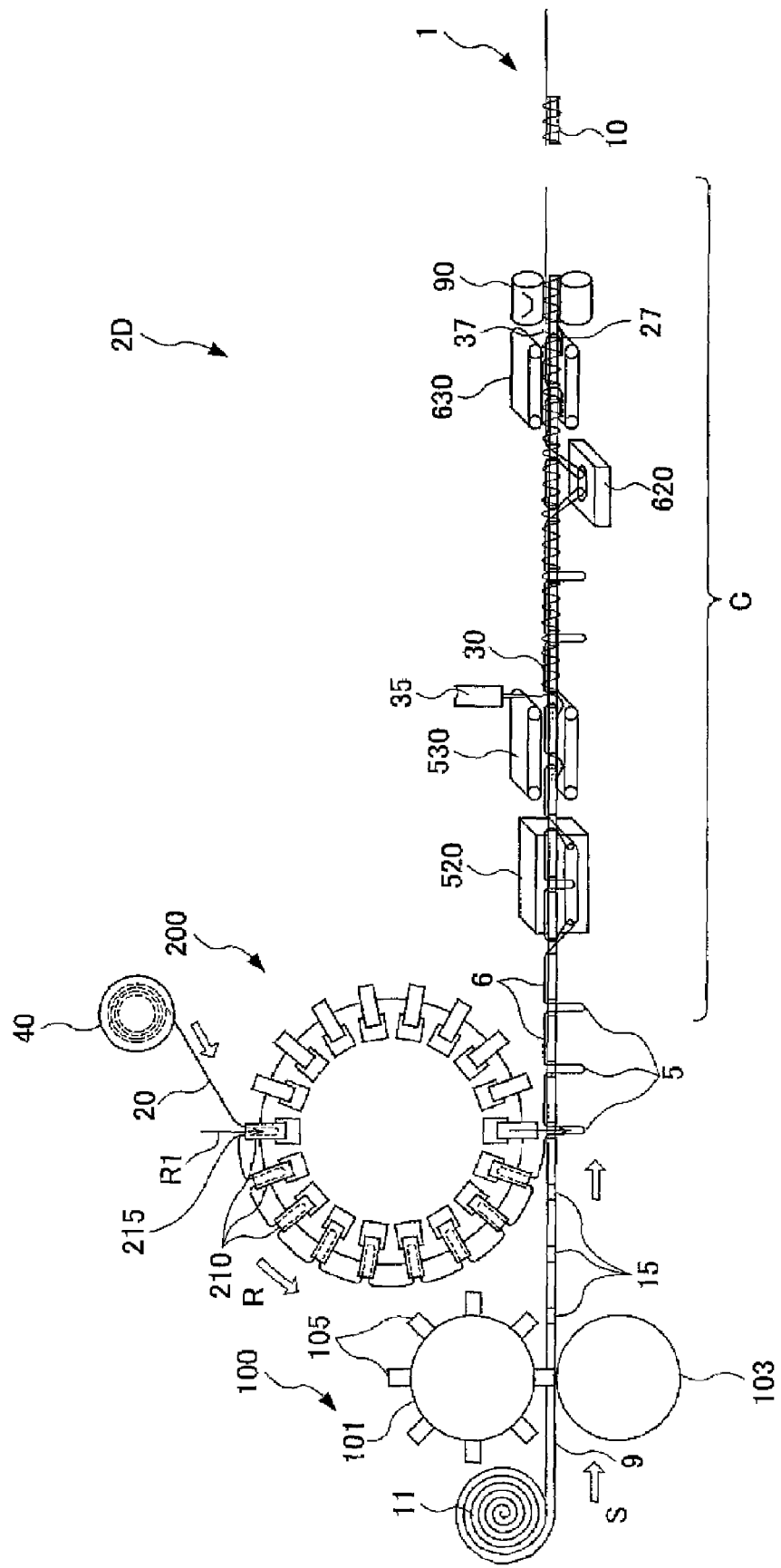
FIG. 12 shows a view describing the fifth embodiment.
Figure 13:
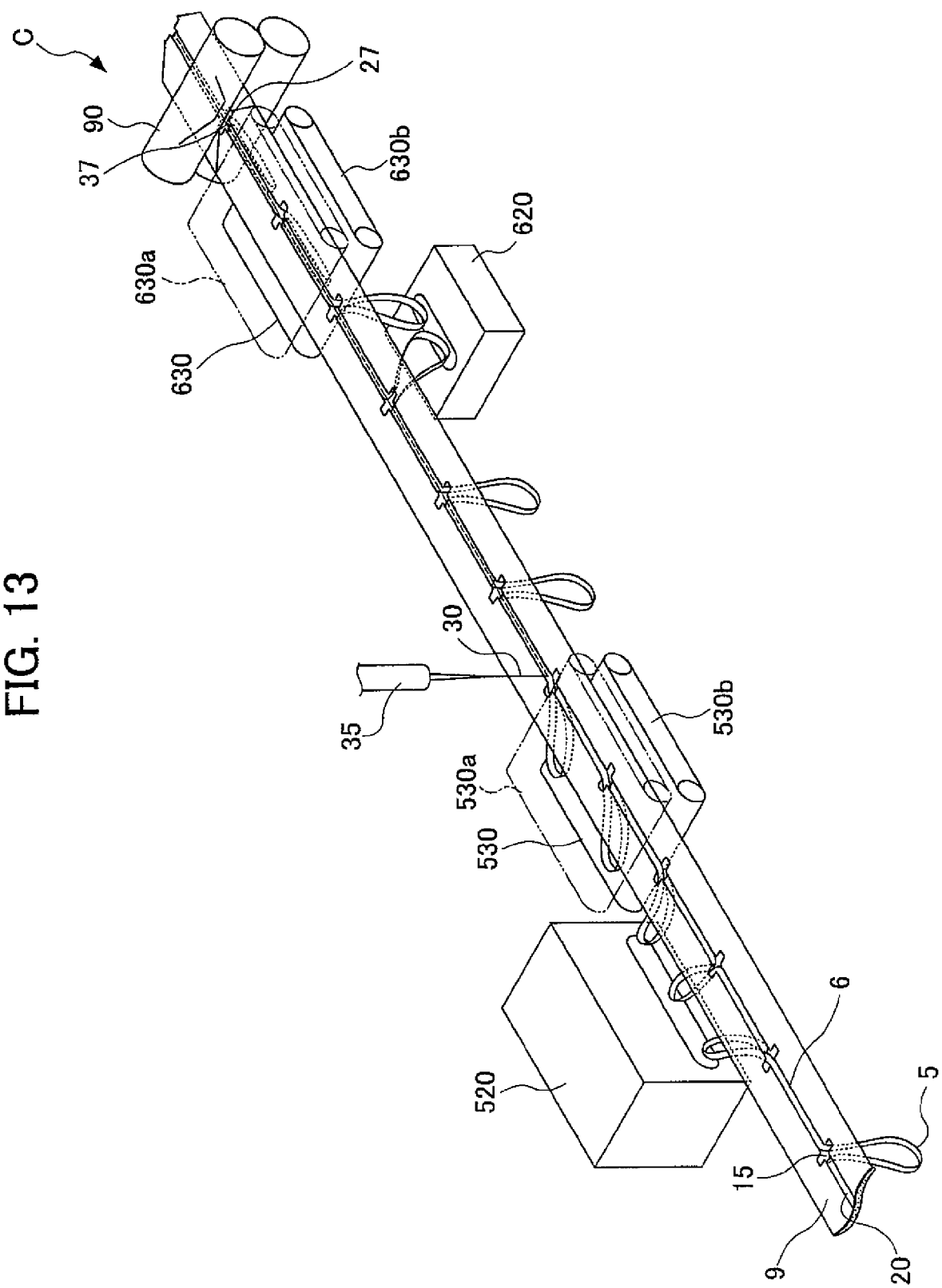
FIG. 13 shows an enlarged view of area C in FIG. 12.

FIG. 1 shows a plan view of the sheet-like structure of Example 1. FIG. 2 shows a cross section of X-X line of FIG. 1. FIG. 3 shows a plan view of a conventional sheet-like structure. FIG. 4 shows a view describing a manufacturing system of the first embodiment of the present invention. FIGS. 5A and 5B show an enlarged view of area A in FIG. 4. FIGS. 6A and 6B show an enlarged view of area B in FIG. 4. FIG. 7 shows a view describing a manufacturing system of the second embodiment of the present invention. FIG. 8 shows a view describing manufacture of sheet-like structures in the manufacturing system of the second embodiment of the present invention. FIG. 9 shows a view describing a manufacturing system of the third embodiment of the present invention. FIG. 10 shows a view describing a manufacturing system of the fourth embodiment of the present invention. FIG. 11 shows a view describing manufacture of sheet-like structures in the manufacturing system of the fourth embodiment of the present invention. FIG. 12 shows a view describing the fifth embodiment. FIG. 13 shows an enlarged view of area C in FIG. 12. FIGS. 14A, 14B and 14C show a view describing manufacture of sheet-like structures in the manufacturing system of the fifth embodiment.

(1) Manufacturing System

The manufacturing system of sheet-like structures according to the present invention will be described referring to FIGS. 1 to 14.

(1.1) Whole System

The whole composition of the manufacturing system of the present invention will be described through sheet-like structures and a manufacturing system of the first embodiment shown in FIGS. 1 to 7.

(1.1.1) Sheet-like Structure

The manufacturing target of the manufacturing system of the present invention is a sheet-like structure comprising a sheet-like member, and a cord member, which is sewn onto a predefined surface of the sheet member with a specified thread member, which has an extended portion extending from an outer edge of the predefined surface, and on which a non-sewn area, without the specified thread member, is formed. For example, as shown in FIG. 1, a sheet-like structure 1 of the first embodiment comprises an absorbing member 10 with a planar feather-like form as a sheet-like member, and a cord member 20, which is sewn onto a predefined surface of the absorbing member 10 with a specified thread member 30, and has an extended portion 21 extending from an outer edge of the predefined surface, on which non-sewn area 22 without the thread member 30 is formed. The sheet-like structure 1 according to the present invention can be used as an absorbing body for tampons.

Specifically, the sheet-like structure 1 comprises the absorbing member 10 with a planar feather-like form, and a cord member 20 in which a part thereof is arranged in contact with a predefined surface of the absorbing member 10 so that it is extended in the longitudinal direction in an approximate center of the width direction of the absorbing member 10 and sewn with the thread member 30 as shown in FIG. 1. The cord member 20, which is longer than the length of the absorbing member 10 in the longitudinal direction, has the extended portion 21 extending from an outer edge of the absorbing member 10 in the longitudinal direction. When the sheet-like structure 1 is used as an absorbing body for tampons, the absorbing member 10 is formed into an approximate cylindrical form by compression, to be placed in an applicator (not shown).

As shown in FIG. 2, the absorbing member 10 as a sheet-like member has an absorbing layer 14 comprising absorbent fiber material, and a surface material 12 with liquid permeability which covers the absorbing layer 14 so as to wrap the absorbing layer 14 in the width direction. The absorbing member 10 as a sheet-like member of the embodiment may have a dimension of total length in the longitudinal direction of 30 mm to 90 mm and total length in the width direction of 30 mm to 70 mm, for example. The absorbing member 10 is acceptable as long as it is in the sheet-like form in the end and the absorbing member 10 may be formed into a sheet-like form by folding as a sailor collar or by crushing a rolled-in cross section structure. Moreover, the planar form is not limited and examples of the planar form of the absorbing member 10 include square, rectangle and oval shape. It is preferable to lengthen the length of the absorbing member 10 as an absorbing body for tampons because it enables reduction of leakage due to the lengthened contact and absorbing length (the length of an area where the absorbing body and the inner wall of vagina come in contact with each other). However, this may be a cause of unpleasant sensation during use and it is more preferable for the absorbing member 10 to be in a feather-like form as shown in FIGS. 1 and 3. More specifically, it is favorable because the amount and density of the fiber can be decreased at both front and back edges of the absorbing body for tampons after forming by compression, while the absorbing member 10 is lengthened to prevent occurrence of unpleasant sensations. In addition, resistance to removal is reduced making it easier to be pulled off after use.

Examples of the absorbent fiber material used for the absorbing layer 14 include hydrophilic fibers such as cotton, rayon and synthetic fiber. Single or multiple fiber webs, nonwoven or woven fabrics, preferably having a weight of 150 g/m$^2$ to 1,500 g/m$^2$ and a thickness of substantially 0.1 mm to 0.9 mm are lapped over another to form an absorbing layer having a thickness of 1.0 mm to 15 mm and preferably having a thickness of 2.0 mm to 10 mm is used as the absorbing layer 14. There are fiber webs and nonwoven fabrics shaped by card webbing, air-laying method, wetlaid method and the like, on a base such as a synthetic fiber sheet. Hydrophobic fibers or hydrophobic fibers provided with a hydrophilic property may also be comprised in the absorbing layer 14 with the hydrophilic fibers. In addition, compounds having a water absorbing property, such as polymers with a high water absorbing property, may be comprised in the absorbing layer 14.

The surface material 12 with liquid permeability is made of nonwoven fabrics formed by hydrophobic fibers or mesh films, to which mesh treatment has been performed. The type of nonwoven fabrics used for the surface material 12 is not particularly limited and examples include spunbond nonwoven fabrics, spunlace nonwoven fabrics and thermal bond nonwoven fabrics. The hydrophobic fiber which makes up the nonwoven fabrics is not particularly limited and examples include fibers of polyester, polypropylene and polyethylene. The weight of the nonwoven fabrics is preferably 8 g/m$^2$ to 40 g/m$^2$. The mesh film is preferably a polyolefin film such as polypropylene or polyethylene.

The cord member 20 is arranged in contact with a predefined surface of the absorbing member 10 so that it is extended in the longitudinal direction in the approximate center of the width direction of the absorbing member 10, and comprises a sewn area 25 sewn with the thread member 30. The cord member 20, which is longer than the length of the absorbing member 10 in the longitudinal direction, has the extended portion 21 extended from an outer edge of the absorbing member 10 in the longitudinal direction.

Strings made of natural or synthetic fibers, resin-made cords, threads of more than predetermined diameter and composite yarns formed by twisting number of above threads can be used as the cord member 20. Composite yarns formed by twisting plural cotton threads or single threads such as polyester threads can be used when making an absorbing body for tampons, for example. The cord member 20 is preferably water repellent finished by attaching paraffin, for example, in order to prevent contamination from outside of the body, such as urine, from being drawn into the cord member during use. The length of the cord member 20 is preferably 110 mm to 250 mm when the length of the absorbing member is 30 mm to 90 mm, for example.

The sewn area 25 and the non-sewn area 22 are formed along the cord member 20 of the sheet-like structure 1 of Example 1 as shown in FIG. 1. The non-sewn area 22 is formed on the extended portion 21. The sewn area 25 comprises the thread member 30 and the non-sewn area 22 does not comprise the thread member 30.

The sewn area 25 is formed on an entire surface or a part of a contact portion 23 where the cord member 20 is in contact with the absorbing member 10, which is a sheet-like member. The sewn area 25 is formed on the entire surface of the contact portion 23 in the first to fifth embodiments described below.

The non-sewn area 22 which does not comprise the thread member 30 is formed on the extended portion 21 as described above. That is, the thread member 30 forming the sewn area 25 is not continued to a free end 26 of the extended portion 21.

Specifically, as shown in FIG. 1, the non-sewn area 22 not sewn with the thread member 30 is formed from an edge of the sewn area 25 to the free end 26 of the extended portion 21 of the sheet-like structure 1 of Example 1.

The thread member 30 is acceptable as long as a member is made of materials which can sew the absorbing member 10 as a sheet member and the cord member 20 together and it is finer than a predetermined diameter. Examples include threads formed by natural materials, threads of synthesized fibers and fine wires. For example, a thread formed by twisting a number of single threads such as cotton threads can be used for the sheet-like structure 1 of Examples 1 and 2. These threads are water repellent finished by attaching paraffin, etc. as necessary.

As shown in FIG. 3, a sewn area 24 is formed on the entire length of the cord member 20 of a conventional sheet-like structure 1A. On the contrary, the entire length of the sewn area 25 relative to the entire length L2 of the cord member 20 in the sheet-like structure 1 of Example 1 may be 16% to 44%, for example.

That is, the sheet-like structure 1 of Example 1 can prevent the thread member 30 from coming off while also preventing liquid leakage because the thread member 30 forming the sewn area 25 is not continued to the free end 26. Furthermore, used amount of the thread member 30 used for the sheet-like structure 1 can be controlled. For example, the used amount of the thread member 30 can be reduced to substantially 16% to 44% as compared to the conventional sheet-like structure 1A as shown in FIG. 3.

This is advantageous in terms of cost. That is, cost of the thread member 30 is reduced. Moreover, the weight of the sheet-like structure 1 can be reduced because used amount of the thread member 30 is reduced. Furthermore, this is significantly advantageous for the manufacturing process because this reduces sewing considerably.

Specifically, the time it takes for sewing can be shortened, thereby shortening the manufacturing time and improving the productivity considerably. For example, productivity can be improved up to substantially 200% to 600% relative to the productivity of the conventional sheet-like structure 1A as shown in FIG. 3.

Moreover, the time taken for sewing or other steps can be lengthened by the time shortened, and the steps are performed more thoroughly, thereby the quality of the sheet-like structures can be improved.

(1.1.2) Outline of Manufacturing System

The manufacturing system (apparatus) 2 of the sheet-like structure 1 of the first embodiment is equipped with a cord member reeling-out unit 40 as a cord member reeling-out apparatus, a roll cutter unit 100 as an inserting portion forming apparatus, a suction drum 200 as a loosened portion forming apparatus as well as an arranging apparatus, a sewing machine unit 35 as a sewing apparatus, belt-like member cutters 110 and 120 as belt-like member cutting apparatuses, a thread member cutter 70 as a thread member cutting apparatus and a cord member cutter 80 as a cord member cutting apparatus as shown in FIG. 4.

(1.2) Cord Member Reeling-Out Apparatus

The cord member reeling-out unit 40 as a cord member reeling-out apparatus reels out the cord member 20 in a predetermined direction as shown in FIG. 4. The cord member 20 is staged in the cord member reeling-out unit 40 in a rolled up condition in a substantially cylindrical form. The cord member 20 can be reeled out by rotating the cylinder around its cylindrical axis. The length of the cord member 20 reeled out from the cord member reeling-out unit 40 can be adjusted by controlling the rotating speed of the cylinder by means of variable speed motors, etc. Meanwhile, the cord member 20 is reeled out while being in contact with openings 215 of cylindrical members 210 in the suction drum 200 as a loosened portion forming apparatus described below.

(1.3) Loosened Portion Forming Apparatus

The suction drum 200 as a loosened portion forming apparatus is equipped with plural cylindrical members 210 formed in a circumferential direction of the suction drum 200 at predetermined intervals as shown in FIG. 4. The plural cylindrical members 210 are hollow cylindrical members having the openings 215 arranged in an outer circumferential direction of the suction drum 200 at predetermined intervals. Air tubes (not shown) are connected to each cylindrical member 210 for adjusting the hollow spaces in the cylindrical members 210 between negatively pressurized and pressurized conditions.

Only a predetermined length of the cord member 20 can be inserted to the hollow space of the cylindrical member 210 by negatively pressurizing the hollow space of the cylindrical member 210 while the cord member 20 reeled out from the above cord member reeling-out unit 40 is in contact with the opening 215 of a predetermined cylindrical member 210 as indicated by R1. By the above procedure, a substantially U-shaped loosened portion 5 can be formed. Moreover, the loosened portions 5 can be formed on the cord member 20 at predetermined intervals by continuously reeling out the cord member 20 from the cord member reeling-out unit 40 and by rotating the suction drum 200 around its cylindrical axis in a direction of an arrow R at a predetermined speed. Meanwhile, although a cylindrical member is used as a member having a prescribed hollow space in the embodiment, it is not limited to the above. For example, flat tube members with ellipsoid cross sections or rectangular-solid members may also be used.

(1.4) Inserting Portion Forming Apparatus

The roll cutter unit 100 as an inserting portion forming apparatus is equipped with a cutting roll 101 on which plural cutting units 105 which form predefined openings 15 are formed, and a planar roll 103 arranged substantially alongside the cutting roll 101 as shown in FIG. 4. The plural cutting units 105 are formed on an outer circumferential surface of the cutting roll 101 in an outer circumferential direction at predetermined intervals. The shapes of the cutting units 105 and intervals in the outer circumferential direction are determined according to the sheet-like structure 1. Specifically, the shapes of the cutting units 105 and intervals in the outer circumferential direction are determined according to the shapes and intervals of the openings 15 formed on the belt-like member 9.

The plural openings 15 can be formed continuously at predetermined intervals by letting the belt-like member 9 through between the cutting roll 101 in the roll cutter unit 100 and the planar roll 103 continuously.

(1.5) Arranging Apparatus

The suction drum 200 as an arranging apparatus is equipped with plural cylindrical members 210 formed in a circumferential direction of the suction drum 200 at predetermined intervals as shown in FIG. 4. As described above, the plural cylindrical members 210 are hollow cylindrical members having the openings 215 arranged in an outer circumferential direction of the suction drum 200 at predetermined intervals. Air tubes (not shown) are connected to each cylindrical member 210 for adjusting the hollow spaces in the cylindrical members 210 between negatively pressurized and pressurized conditions.

A substantially U-shaped loosened portion 5 formed by pulling a predetermined length of the cord member 20 into the hollow space of the cylindrical member 210 as indicated by R1 can be pushed out from the opening 215 of the cylindrical member 210 by pressurizing the hollow space of the cylindrical member 210 as indicated by R2. Specifically, as shown in FIG. 4, the hollow space in the cylindrical member 210 is pressurized while the opening 215 of the cylindrical member 210 is in contact with the opening 15 formed on the belt-like member 9. By the above procedure, the loosened portion 5 is pushed out from the cylindrical member 210 as indicated by R2 and inserted to the opening 15 to be arranged on a surface opposite of the surface with which the cylindrical member 210 is in contact.

Plural linear portions 6 are formed by arranging the cord member 20 which connects each of the plural loosened portions almost linearly along the surface with which the cylindrical member 210 is in contact. The plural linear portions 6 are arranged almost linearly in an approximate center in the width direction of the belt-like member 9. The sewn areas 25 are then formed on the portions (not shown) of each linear portion 6 which comes in contact with the belt-like member 9 by sewing along the straight line by means of the sewing unit 35 as a sewing apparatus.

(1.6) Sewing Apparatus

The sewing unit 35 as a sewing apparatus sews each of the plural linear portions 6 and the belt-like member 9 together by a thread member 30. That is, the plural linear portions 6 arranged almost linearly on a predefined surface of the belt-like member 9 are sewn continuously from upper surfaces of the linear portions 6 with the thread member 30 as shown in FIGS. 4 and 5.

Specifically, the plural linear portions 6 are sent forth continuously along the straight line formed by the plural linear portions 6 to a sewing position of the fixed sewing unit 35.

Sewing is performed continuously by the sewing unit 35 with the thread member 30. By this, sewn areas 25 can be formed on the contact portions 23 of the linear portions 6 with which the belt-like member 9 is in contact. Furthermore, thread connecting portions 37, which are parts of the thread member 30, are formed so as to connect specified linear portion 6 and the linear portions 6 which lie adjacent to the specified linear portion 6.

Moreover, the sewing apparatus may further comprise a primary evacuating apparatus (not shown) which evacuates each of the plural loosened portions 5 so as not to be overlapped with the straight line formed by the plural linear portions 6. For example, when a loosened portion 5 is arranged on a lower surface of the belt-like member 9, being overlapped with the straight line, and sewing is performed by the sewing unit 35, the loosened portion 5 is sewn onto the belt-like member 9. In order to avoid this, the loosened portion 5 can be pulled to the side in the width direction of the belt-like member 9 by predetermined members, etc. In this way, the loosened portions 5 can be evacuated in order to avoid overlapping with the straight line. Other primary evacuating apparatus may be exemplified by the primary evacuating apparatuses described in the second to fifth embodiments.

(1.7) Belt-Like Member Cutting Apparatus

The belt-like member cutting apparatus forms plural absorbing members 10 as sheet members by cutting the belt-like member 9 in prescribed forms so as for the specified linear portion 6 sewn by the sewing unit 35 and the linear portions 6 which lie adjacent to the specified linear portion 6 are arranged on the different absorbing members 10. Specifically, as shown in FIGS. 4 and 6, the belt-like member cutter 110 as a belt-like member cutting apparatus cuts the belt-like member 9 from one side to an edge of the opening 15. The belt-like member cutter 120 then cuts the belt-like member 9 from the other side to the edge of the opening 15. Because the linear portion 6 are arranged between each of openings, by conducting the cutting continuously, the belt-like member 9 is cut in prescribed forms to form plural absorbing members 10 so that the linear portions 6, each of which are arranged between the openings 15 and lie adjacent to each other, are arranged on the different absorbing member 10.

Moreover, a secondary evacuating apparatus which evacuates a cord connecting portion 27 from the cutting position where the belt-like member 9 is cut by the belt-like member cutters 110 and 120 may be provided. For example, the cord connecting portion 27 can be pulled to the side in the width direction which is opposite to the cutting position to be evacuated by means of movable guides 55 and 56 shown in FIGS. 6A and 6B. The movable guides 55 and 56 are arranged so as to be movable in the width direction of the belt-like member 9 by means of a driving unit (not shown). Other secondary evacuating apparatuses may be exemplified by the secondary evacuating apparatuses described in the second to fifth embodiments.

(1.8) Thread Member Cutting Apparatus

The thread member cutter 70 as a thread member cutting apparatus cuts thread connecting portions 37 which are parts of the thread member 30 formed so as to connect between each of the plural linear portions 6 which lie adjacent to each other as shown in FIGS. 4 and 5.

Various cutter members may be used as thread member cutters 70. For example, cutters with a width narrower than the width of the openings 15 as shown in FIG. 5 or roll cutter members (not shown) may be used. The distance between each absorbing member 10 can be adjusted by cutting the thread member 30 making up the thread connecting portions 37 by means of the thread member cutter 70, making it possible to extend the cord member 20 forming the cord connecting portions 27 almost linearly.

(1.9) Cord Member Cutting Apparatus

As shown in FIGS. 4 and 6, a cord member cutter 80 as a cord member cutting apparatus cuts cord connecting portions 27, which are parts of the cord member 20 formed so as to connect a predetermined absorbing member 10 of the plural absorbing members 10 and absorbing members 10 which lie adjacent to the predetermined absorbing member 10, at a predetermined position. The distance between the predetermined absorbing member 10 and its adjacent absorbing member 10 is lengthened while the cord connecting portion 27 is lengthened almost linearly because the thread member 30 which makes up the thread connecting portions 37 is already cut by the thread member cutter 70, thereby enabling cutting of the cord member 20 while the cord connecting portions 27 are lengthened almost linearly.

(1.10) Belt-like Member Forming Apparatus

The absorbing member 10 as a sheet member of the first embodiment is a sheet-like absorbing member 10 comprising a predetermined absorbing layer 14 with liquid absorbability, coated with a surface material 12 of thin film form. Similarly, the belt-like member 9, which is a material of the absorbing member 10 as a sheet member, is a belt-like absorbing member comprising a predetermined absorbing layer 14 with liquid absorbability, coated with a surface material 12 of thin film form. The manufacturing system of sheet-like structures 2 of the first embodiment may be equipped with a belt-like member forming apparatus by which the absorbing layer 14 (not shown) is coated with the surface material 12 of thin film form. Examples of the belt-like member forming apparatus include a specific apparatus by which the absorbing layer 14 with a prescribed form is coated so as to be wrapped with the surface material 12 having a width longer than the outer circumference in a short side direction of the absorbing layer 14.

Furthermore, the belt-like member 9 can be formed by combining an apparatus by which the absorbing layer 14 is coated so as to be wrapped with the surface material 12 having a width longer than the outer circumference in a short side direction of the absorbing layer 14, and an apparatus such as specific emboss rolls which artificially combine the surface material 12 and the absorbing layer 14 to be formed into an approximate sheet form by heating and pressurizing while the surface of the absorbing layer 14 is coated with the surface material 12.

(1.11) Others

When the sheet-like structure 1 of the first embodiment is used as an absorbing body for tampons, a compressing apparatus (not shown) by which the absorbing member 10 is compressed to be inserted into a prescribed applicator may be further included.

(2) Second Embodiment

The manufacturing system of sheet-like structures 2A according to the second embodiment is similar to the manufacturing system of sheet-like structures 2 according to the first embodiment as shown in FIGS. 7 and 8. The manufacturing system of sheet-like structures 2A according to the second embodiment will be described below with a focus on differences from the manufacturing system of sheet-like structures 2 according to the first embodiment.

A roll cutter unit 115 works as an inserting portion forming apparatus as well as a belt-like member forming apparatus. Openings 15 are formed on a belt-like member 9 reeled out from a belt-like member reeling-out unit 11 while cut portions continued from the edges of the openings 15 are formed.

Loosened portions 5 inserted into the openings 15 are pulled to a side in the same width direction as the cut portions formed in advance while being sandwiched by a conveyer 500 which works as a first evacuating apparatus as well as a second evacuating apparatus. Sewing is performed by a sewing unit 35 while the loosened portions 5 are being pulled to the side and the belt-like member 9 is cut from the sides opposite of the cut portions formed in advance to the edges of the openings 15 by a roll cutter unit 125 as a belt-like member cutting apparatus and in addition, a thread member 30 forming thread connecting portions 37 are cut by a roll cutter unit 75 as a thread member cutting apparatus.

A sheet-like structure 1 can be obtained by cutting a cord member 20 forming the thread connecting portions 37 by a roll cutter unit 85.

(3) Third Embodiment

The manufacturing system of sheet-like structures 2B according to the third embodiment is similar to the manufacturing system of sheet-like structures 2A according to the second embodiment as shown in FIG. 9. The manufacturing system of sheet-like structures 2B according to the third embodiment will be described below with a focus on differences from the manufacturing system of sheet-like structures 2A according to the second embodiment.

A roll cutter unit 115 works as an inserting portion forming apparatus as well as a belt-like member forming apparatus. Openings 15 are formed on a belt-like member 9 reeled out from a belt-like member reeling-out unit 11 while cut portions continued from the edges of the openings 15 are formed.

Loosened portions 5 inserted into the openings 15 are pulled to a side in a width direction of a belt-like member 9 while being sandwiched by a conveyer 510 as a first evacuating apparatus. Sewing is performed by a sewing unit 35 while the loosened portions 5 are being pulled to the side.

The sewn belt-like member 9 is twisted in a way so that the cut portions, formed at predetermined positions in advance, are arranged on the lower side. In this way, the loosened portions 5 are arranged on the same side as the cut portions formed in advance by gravitational force.

The belt-like member 9 is cut from the sides opposite of the cut portion formed in advance, to the edges of the openings 15, by a roll cutter unit 125 as a belt-like member cutting apparatus. The roll cutter unit 125 is tilted corresponding to the belt-like member 9.

Furthermore, a sheet-like structure 1 can be obtained by cutting a thread member 30 forming the thread connecting portions 37 by a roll cutter unit 75 as a thread member cutting apparatus, and by cutting a cord member 20 forming the thread connecting portions 37 by a roll cutter unit 85.

(4) Fourth Embodiment

The manufacturing system of sheet-like structures 2C according to the fourth embodiment is similar to the manufacturing system of sheet-like structures 2A according to the second embodiment as shown in FIGS. 10 and 11. The manufacturing system of sheet-like structures 2C according to the fourth embodiment will be described below with a focus on differences from the manufacturing system of sheet-like structures 2A according to the second embodiment.

A roll cutter unit 115 works as an inserting portion forming apparatus as well as a belt-like member forming apparatus. Openings 15 are formed on a belt-like member 9 reeled out from a belt-like member reeling-out unit 11 while cut portions continued from the edges of the openings 15 are formed.

Loosened portions 5 inserted into the openings 15 are pulled to a side in a width direction of the belt-like member 9 opposite of the cut portions formed in advance while being formed into a U shape by plural movable guides 57 which work as a first evacuating apparatus as well as a second evacuating apparatus. Sewing is performed by a sewing unit 35 while the loosened portions 5 are being pulled to the side and the belt-like member 9 is cut from the sides opposite of the cut portions formed in advance to the edges of the openings 15 by a roll cutter unit 125 as a belt-like member cutting apparatus.

The inner sides of the U-shaped loosened portions 5 formed by the movable guides 57 are cutting positions of the roll cutter unit 125 as shown in FIG. 11. The loosened portions 5 are positioned by the movable guides 57 and the inner sides of the U-shaped loosened portions 5 are determined as cutting positions.

Furthermore, a sheet-like structure 1 can be obtained by cutting a thread member 30 forming the thread connecting portions 37 by a roll cutter unit 75 as a thread member cutting apparatus, and by cutting a cord member 20 forming the thread connecting portions 37 by a roll cutter unit 85.

(5) Fifth Embodiment

As shown in FIGS. 12 to 14, the manufacturing system of sheet-like structures 2D according to the fifth embodiment is similar to the manufacturing system of sheet-like structures 2 according to the first embodiment. The manufacturing system of sheet-like structures 2D according to the fifth embodiment is characterized by having a roll cutter unit 90 which makes up a belt-like member cutting apparatus, a thread member cutting apparatus and a cord member cutting apparatus. In other words, it is characterized by being able to cut a belt-like member 9, a thread member 30 and a cord member 20 simultaneously. The manufacturing system of sheet-like structures 2D according to the fifth embodiment will be described below with a focus on differences from the manufacturing system of sheet-like structures 2 according to the first embodiment.

Loosened portions 5 inserted into the openings 15 by a suction drum 200 as an arranging apparatus are pulled to a side in a width direction of the belt-like member 9 by a first suction box 520 making up a first evacuating apparatus placed on the side of the belt-like member 9 as shown in FIGS. 12 and 13. The loosened portions 5 are moved in a predetermined direction while being pulled to the side and sandwiched by a conveyer 530 which makes up the first evacuating apparatus.

The cord member 20 is sewn onto the belt-like member 9 by a sewing machine unit 35 as a sewing apparatus while the loosened portions 5 are being pulled to the side by the conveyer 530. After sewing, cord connection portions 27 are freed from the conveyer 530 and placed so as to be hanged almost vertically on the lower side of the belt-like member 9.

A second suction box 620 which makes up a conveying apparatus is placed on the lower side of the belt-like member 9. The cord connecting portions 27 are drawn from the lower side of the belt-like member 9 by the second suction box 620 placed on the lower side of the belt-like member 9. The leading ends of the cord connecting portions 27 are pulled by the second suction box 620 to remain at a certain position while the sides sewn onto the belt-like member 9 are moved in a specific direction. In this way, the cord connecting portions 27 are tilted relative to the vertical direction. The cord connecting portions 27 are then sandwiched by a conveyer 630 which makes up a conveying apparatus while being placed along the longitudinal direction of the belt-like member 9. As shown in FIGS. 14A, 14B and 14C, the cord connecting portions 27 are placed so that the cord connecting portions 27 cross over the openings 15 in a longitudinal direction of the belt-like member 9 together with thread connecting portions 37.

The belt-like member 9 is cut at positions including the openings 15 by the roll cutter unit 90 which works as a belt-like member cutting apparatus, a thread member cutting apparatus and a cord member cutting apparatus. Stated another way, the belt-like member 9, the thread member 30 and the cord member 20 are cut simultaneously by the roll cutter unit 90. A sheet-like structure 1 can be obtained as described above.

The first suction box 520 which makes up the first evacuating apparatus is equipped with a suction unit formed on a side surface of the suction box 520. The suction box 520 is positioned so that the suction unit faces the belt-like member 9. The leading ends of the loosened portions 5 are drawn in by the suction unit of the first suction box 520 to be pulled to a certain side in a width direction.

The conveyer 530 which makes up the first evacuating apparatus comprises an upper conveyer 530a and a lower conveyer 530b, as shown in FIG. 13. The loosened portions 5 pulled to the side by the suction box 520 as described above are sandwiched by the upper and lower conveyers 530a and 530b of the conveyer 530 while still being pulled to the side. In this way, the loosened portions 5 can be moved in a predetermined direction while being pulled to the side.

The second suction box 620 which makes up the conveying apparatus is equipped with a suction unit formed on an upper side of the second suction box 620. The leading ends of the cord connecting portions 27 are drawn in by the suction unit of the second suction box 620 to remain at a certain position while the sides of the cord connecting portions 27 sewn onto the belt-like member 9 are moved in a predetermined direction to be wholly tilted relative to the vertical direction.

The conveyer 630 which makes up the conveying apparatus comprises an upper conveyer 630a and a lower conveyer 630b as shown in FIG. 13. The cord connecting portions 27 which are tilted relative to a vertical direction by the second suction box 620 are sandwiched by the upper and lower conveyers 630a and 630b of the conveyer 630. In this way, the cord connecting portions 27 are sandwiched while being placed along the longitudinal direction of the belt-like member 9. The cord connecting portions 27 are placed along the longitudinal direction of the belt-like member 9 in a way so that the cord connecting portions 27 cross over the openings 15 in the longitudinal direction of the belt-like member 9 together with the thread connecting portions 37.

The roll cutter unit 90 which makes up the belt-like member cutting apparatus, the thread member cutting apparatus and the cord member cutting apparatus are a roll cutter with a convex blade with a predetermined form disposed on a surface of the roll. The convex blade is formed on the roll cutter unit 90 of the fifth embodiment for cutting the belt-like member 9 in a width direction at one time. The cutting positions of the roll cutter unit 90 include the openings 15. Stated another way, the convex blade of the roll cutter unit 90 is formed so that the convex blade can cut the openings 15, from an edge in a width direction of the openings 15 to the side of an edge of the belt-like member 9 and from another edge in the width direction of the openings 15 to the side of another edge of the belt-like member 9. In this way, the roll cutter unit 90 can cut the belt-like member 9 as well as the thread connecting portions 37 and the cord connecting portions 27 which are arranged so as to cross over the openings 15. Because the roll cutter unit 90 of the fifth embodiment cuts the belt-like member 9, the thread member 30 and the cord member 20 simultaneously, the shapes of the openings 15 are not limited as long as they can be inserted to the cord member 20. Although the openings 15 are formed substantially in form of a cross in the fifth embodiment as shown in FIG. 13, the openings 15 may be formed substantially in form of a straight line (rectangle) extended in a width direction of the belt-like member 9, for example.

(6) Method for Manufacturing

The method for manufacturing a sheet-like structure of the present invention that comprises a sheet member with a prescribed form, and a cord member sewn onto a predefined surface of the sheet member with a specified thread member, which has an extended portion extending from an outer edge of the predefined surface, on which non-sewn area, without the specified thread member, is formed, includes: forming a loosened portion wherein plural loosened portions, which are substantially U-shaped, are formed on a cord member, forming an inserting portion wherein plural cut portions or openings are formed on the belt-like member with an approximate belt form through which the loosened portions can be inserted, arranging wherein each of the plural loosened portions is inserted to each of the plural cut portions or openings from a predefined surface of the belt-like member to an opposite surface of the predefined surface of the belt-like member, and plural linear portions are formed almost linearly on a predefined surface which connect plural loosened portions respectively, sewing wherein each of the plural linear portions arranged in the arranging and a belt-like member are sewn together with a thread member, cutting a belt-like member wherein plural sheet members are formed by cutting the belt-like member in prescribed forms so as for a specified linear portion of the plural linear portions sewn in the sewing and linear portions which lie adjacent to the specified linear portion are arranged on the different sheet members, cutting a thread member wherein thread connecting portions, which are parts of the thread member formed so as to connect a specified linear portion of the plural linear portions sewn in the sewing and other linear portions which lie adjacent to the specified linear portion, are cut, and cutting a cord member wherein cord connecting portions, which are parts of the cord member formed so as to connect a specified linear portion of the plural linear portions sewn in the sewing and other linear portions which lie adjacent to the specified linear portion, are cut at a predetermined position.

The manufacturing target of the method for manufacturing according to the present invention is a sheet-like structure comprising a sheet member with a prescribed form and a cord member, which is sewn onto a predefined surface of the sheet member, with a specified thread member, having an extended portion extending from an outer edge of the predefined surface on which non-sewn area, without the specified thread member, is formed. The sheet member of the sheet-like structure is an approximate sheet-like member made of a material on which cord members can be sewn with a specified thread member, and examples include fabric members, rubber members, and sheet-like absorbing members which make up the above-mentioned absorbing member for tampons. The cord member sewn onto the sheet member is made of a material which can be sewn onto the sheet members, and examples include strings made of natural or synthesized fibers, resin-made cords, threads of more than predetermined diameter and composite yarns formed by twisting a number of the above threads. Moreover, the thread member is finer than a predetermined diameter, formed of a material in which the sheet member and the cord member can be sewn together, and examples include threads formed of natural materials, threads of synthesized fibers and fine wires.

In the step of forming the loosened portion, plural loosened portions, which are substantially U-shaped, are formed on a cord member reeled out from a thread supplying unit in which thread members are winded up, for example. These loosened portions become extended portions in the sheet-like structure and the linear portions described below become portions sewn onto the sheet member.

In the step of forming the inserting portion, plural cut portions or openings are formed on the belt-like member by predetermined cutters, through which loosened portions can be inserted, for example. Inserting the loosened portion means the cord members which are forming loosened portions can be inserted, and configurations during insertion are not limited.

In the step of arranging, each of the plural loosened portions is inserted to the respective plural cut portions or openings from a predefined surface of the belt-like member through an opposite surface of the predefined surface of the belt-like member. An apparatus which can press the loosened portions into cut portions or openings, is usable, for example. In addition, plural linear portions formed almost linearly on a predefined surface connecting the plural loosened portions are respectively formed in the step of arranging. Linear portions are arranged along the surface opposite of the loosened portions inserted from the openings, etc. The plural linear portions arranged as above can be sewn onto the belt-like member continuously in the step of sewing, described below.

In the step of sewing, each of the plural sheet members, that are arranged in the step of arranging, and a belt-like member are sewn together, with a thread member. For example, belt-like members and a cord member are sewn together by sewing along the cord member, arranged on predefined surfaces of the belt-like members, in turn by means of a specified sewing machine, while loosened portions of the cord member are not sewn. In this way, non-sewn areas can be formed on the cord member which make up the loosened portions that will be the extended portions.

In the step of cutting the belt-like member, plural sheet members are formed by cutting the belt-like member in prescribed forms, as for the specified linear portion of the plural linear portions sewn in the step of sewing, and the linear portions which lie adjacent to the specified linear portion are arranged on the different sheet members. Sheet members which make up the sheet-like structure are formed in the step of cutting the belt-like member. The belt-like member is a material of the sheet members.

The belt-like member is cut at a position between a specified linear portion and linear portions which lie next to the specified linear portion in a longitudinal direction of the belt-like member to make sheet members with prescribed forms in the step of cutting the belt-like member so that the specified linear portion sewn in the step of sewing and linear portions which lie adjacent to the specified linear portion are arranged on the different sheet members. The belt-like member may be cut at once or in several batches, in the step of cutting the belt-like member. The belt-like member may be cut in the step of cutting the belt-like member before, after, or at the same time as the thread-connecting portion or cord-connecting portion are cut in a step of cutting the thread member or a step of cutting the cord member.

The thread connecting portions, which are parts of a thread member formed so as to connect the specified linear portion and other linear portions which lie adjacent to the specified linear portion, are cut in the step of cutting the thread member. In addition, cord connecting portions, which are parts of a cord member formed so as to connect a specified linear portion of the plural linear portions sewn by the sewing apparatus and other linear portions which lie adjacent to the specified linear portion, are cut at a predetermined position in the step of cutting the cord member. As described above, cutting of the thread connecting portions in the step of cutting the thread member or cutting of the cord connecting portions in the step of cutting the cord member may be performed before, after, or at the same time as the cutting of the belt-like member in the step of cutting the belt-like member.

Examples of the cutting apparatuses used in the step of cutting the belt-like member, cutting the thread member or cutting the cord member, include specified cutter members and roll members with a convex blade formed on a predefined surface thereof.

Each of the plural cut portions or openings can be formed in an approximate center in a width direction of the belt-like member in the step of forming the inserting portion in the method for manufacturing according to the present invention.

The plural loosened portions are formed by drawing in the plural predetermined portions of the cord member in the step of forming the loosened portion, and each of the plural loosened portions is pushed out with air and inserted to each of the plural cut portions or openings from a predefined surface of the belt-like member to an opposite surface of the predefined surface in the step of arranging in the method for manufacturing according to the present invention. In this way, the loosened portions can be formed and inserted by an apparatus using air pressure.

The plural linear portions are arranged substantially linearly in the step of arranging, and each of the plural linear portions arranged substantially linearly in the step of arranging are sewn continuously onto the belt-like member along the straight line formed by the plural linear portions in the step of sewing in the method for manufacturing of the present invention. In this way, sewing can be performed easily and precise sewing can be performed continuously in the step of sewing.

The step of sewing in the method for manufacturing of the present invention further comprises a step of primary evacuating wherein each of the plural loosened portions are evacuated to avoid overlapping with the straight line formed by the plural linear portions. In this way, the loosened portions can be protected from being sewn onto the sewn areas formed along the straight line formed by the plural linear portions in the step of sewing.

The step of cutting the belt-like member in the method for manufacturing of the present invention comprises a step of secondary evacuation wherein the cord connecting portion is evacuated from a cutting position, where the belt-like member is cut by a predetermined cutting unit. In this way, the cord connecting portions can be protected from being cut at undesired positions when the belt-like member is cut at predetermined positions.

In the method for manufacturing of the present invention, the steps of cutting the belt-like member, the thread member, and the cord member are performed by the same cutting unit, and the cord connecting portion is moved to a cutting position in the cutting unit by a predetermined conveying apparatus. In this way, the belt-like member, the thread member and the cord member can be cut by the cutting unit simultaneously.

The method for manufacturing in the present invention further comprises a step of forming the sheet member in which absorbing layers are coated with surface materials. In this way, a belt-like absorbing member can be formed by applying a surface material to the fibrous absorbing layer for preventing unraveling of the fibrous absorbing layer, and the above-mentioned cord member can be sewn onto the absorbing member formed into a belt-like form.

The method for manufacturing a sheet-like structure of the present invention can be implemented by the above-mentioned manufacturing system (apparatus) of sheet-like structures. The details and operations of each apparatus in each step for implementing the method for manufacturing a sheet-like structure of the present invention are as described in the description of the manufacturing system of sheet-like structures of the present invention above.

The manufacturing system and the method for manufacturing sheet-like structures of the present invention can be used for manufacturing sheet-like structures such as clothes, covers, tents, and absorbing media for tampons.

What is claimed is:

1. A manufacturing system for a tampon comprising a sheet member and a cord member that is sewn onto a surface of the sheet member with a thread member and includes an extended portion extending from an outer edge of the surface, the extended portion having a non-sewn area without the thread member, the manufacturing system comprising:
   a loosened portion forming apparatus to form a plurality of substantially U-shaped loosened portions for a cord member;
   an inserting portion forming apparatus to form plural cut portions or openings for a belt-like member through which the plurality of loosened portions can be inserted;
   an arranging apparatus to insert each of the plurality loosened portions through each of the plural cut portions or each of the plural openings from a first surface to a second surface of the belt-like member opposite to each other, and to arrange a plurality linear portions of the cord member connecting the plurality of loosened portions with each other substantially linearly on a predetermined surface of the belt-like member;
   a sewing apparatus to sew each of the plurality of linear portions of the cord member arranged by the arranging apparatus and the belt-like member together using a thread member,
   a belt-like member cutting apparatus to cut the belt-like member to form a plurality of sheet members in a prescribed shape so that a first linear portion and a second linear portion adjacent to each other in the plurality of linear positions sewn by the sewing apparatus are arranged to be separate on adjacent sheet members;
   a thread member cutting apparatus to cut a thread member connecting portion of the thread member that lies between the first linear portion and the second linear portion; and
   a cord member cutting apparatus to cut a cord connecting portion that connects the first linear portion and the second linear portion, at a predetermined position.

2. The manufacturing system according to claim 1, wherein the inserting portion forming apparatus is capable of forming each of the plural cut portions or opening at a substantially central position in a width direction of the belt-like member.

3. The manufacturing system according to claim 1, wherein the loosened portions forming apparatus draws a predetermined portion of the cord member to form each of the plurality of loosened portions, and the arranging apparatus applies pressurized air to each of the plurality of loosened portions so as to insert each of the plurality of loosened portions into each of the plural cut portions or openings from the first surface to the second surface of the belt-like member opposite to each other.

4. The manufacturing system according to claim 1, wherein the arranging apparatus allows the plurality of linear portions to be substantially aligned in a line, and
   the sewing apparatus sews each of the plurality of linear portions aligned y the arranging apparatus continuously onto the belt-like member along a straight line formed by the plurality of linear portions.

5. A manufacturing system for a sheet-like structure comprising a sheet member and a cord member that is sewn onto a surface of the sheet member with a thread member and has an extended portion extending from an outer edge of the surface, the extended portion having a non-sewn area without the thread member, the manufacturing system comprising:
   a loosened portion forming apparatus to form a plurality of substantially U-shaped loosened portions for a cord member;
   an inserting portion forming apparatus to form plural cut portions or openings for a belt-like member through which the plurality of loosened portions can be inserted;
   an arranging apparatus to insert each of the plurality of loosened portions through each of the plural cut portions or each of the plural openings from a first surface to a second surface of the belt-like member opposite to each other, and to arrange a plurality of linear portions of the cord member connecting the plurality of loosened portions with each other substantially linearly on a predetermined surface of the belt-like member;
   a sewing apparatus to sew each of the plurality of linear portions of the cord member arranged by the arranging apparatus and the belt-like member together using a thread member,
   a belt-like member cutting apparatus to cut the belt-like member to form a plurality of sheet members in a prescribed shape so that a first linear portion and a second linear portion adjacent to each other in the plurality of linear portions sewn by the sewing apparatus are arranged to be separate on adjacent sheet members;
   a thread member cutting apparatus to cut a thread member connecting portion of the thread member that lies between the first linear portion and the second linear portion; and
   a cord member cutting apparatus to cut a cord connecting portion that connects the first linear portion and the second linear portion, at a predetermined position,
   wherein the arranging apparatus allows the plurality of linear portions to be substantially aligned in a line, and the sewing apparatus sews each of the plurality of linear portions aligned by the arranging apparatus continuously onto the belt-like member along a straight line formed by the plurality of linear portions, and
   wherein the sewing apparatus further comprises a first evacuating apparatus to allow each of the plurality of loosened portions to avoid overlapping the straight line formed by the plurality of linear portions.

6. A manufacturing system for a sheet-like structure comprising a sheet member and a cord member that is sewn onto a surface of the sheet member with a thread member and has an extended portion extending from an outer edge of the surface, the extended portion having a non-sewn area without the thread member, the manufacturing system comprising:
a loosened portion forming apparatus to form a plurality of substantially U-shaped loosened portions for a cord member;
an inserting portion forming apparatus to form plural cut portions or openings for a belt-like member through which the plurality of loosened portions can be inserted;
an arranging apparatus to insert each of the plurality of loosened portions through each of the plural cut portions or each of the plural openings from a first surface to a second surface of the belt-like member opposite to each other, and to arrange a plurality of linear portions of the cord member connecting the plurality of loosened portions with each other substantially linearly on a predetermined surface of the belt-like member;
a sewing apparatus to sew each of the plurality of linear portions of the cord member arranged by the arranging apparatus and the belt-like member together using a thread member,
a belt-like member cutting apparatus to cut the belt-like member to form a plurality of sheet members in a prescribed shape so that a first linear portion and a second linear portion adjacent to each other in the plurality of linear portions sewn by the sewing apparatus are arranged to be separate on adjacent sheet members;
a thread member cutting a apparatus to cut a thread member connecting portion of the thread member that lies between the first linear portion and the second linear portion; and
a cord member cutting apparatus to cut a cord connecting portion that connects the first linear portion and the second linear portion, at a predetermined position,
wherein the belt-like member cutting apparatus comprises a cutting unit and a second evacuating apparatus to allow the cord connecting portion to stay away from a cutting position at which the belt-like member is cut by the cutting unit.

7. A manufacturing system for a sheet-like structure comprising a sheet member and a cord member that is sewn onto a surface of the sheet member with a thread member and has an extended portion extending from an outer edge of the surface, the extended portion having a non-sewn area without the thread member,
the manufacturing system comprising:
a loosened portion forming apparatus to form a plurality of substantially U-shaped loosened portions for a cord member;
an inserting portion forming apparatus to form plural cut portions or openings for a belt-like member through which the plurality of loosened portions can be inserted;
an arranging apparatus to insert each of the plurality of loosened portions through each of the plural cut portions or each of the plural openings from a first surface to a second surface of the belt-like member opposite to each other, and to arrange a plurality of linear portions of the cord member connecting the plurality of loosened portions with each other substantially linearly on a predetermined surface of the belt-like member;
a sewing apparatus to sew each of the plurality of linear portions of the cord member arranged by the arranging apparatus and the belt-like member together using a thread member,
a belt-like member cutting apparatus to cut the belt-like member to form a plurality of sheet members in a prescribed shape so that a first linear portion and a second linear portion adjacent to each other in the plurality of linear portions sewn by the sewing apparatus are arranged to be separate on adjacent sheet members;
a thread member cutting apparatus to cut a thread member connecting portion of the thread member that lies between the first linear portion and the second linear portion; and
a cord member cutting apparatus to cut a cord connecting portion that connects the first linear portion and the second linear portion, at a predetermined position, wherein
the belt-like member cutting apparatus, the thread member cutting apparatus, and the cord member cutting apparatus are integrated into one cutting unit, and
further comprises a conveying apparatus for moving the cord connecting portion to a cutting position provided in the cutting unit.

8. A manufacturing system for a sheet-like structure comprising a sheet member and a cord member that is sewn onto a surface of the sheet member with a thread member and has an extended portion extending from an outer edge of the surface, the extended portion having a non-sewn area without the thread member,
the manufacturing system comprising:
a loosened portion forming apparatus to form a plurality of substantially U-shaped loosened positions for a cord member;
an inserting portion formed apparatus to form plural cut portions or openings for a belt-like member through which the plurality of loosened portions can be inserted;
an arranging apparatus to insert each of the plurality of loosened portions through each of the plural openings from a first surface to a second surface of the belt-like member opposite to each other, and to arrange a plurality of linear portions of the cord member connecting the plurality of loosened portions with each other substantially linearly on a predetermined surface of the belt-like member;
a sewing apparatus to sew each of the plurality of linear portions of the cord member arranged by the arranging apparatus and the belt-like member together using a thread member,
a belt-like member cutting apparatus to cut the belt-like member to form a plurality of sheet members in a prescribed shape so that a first linear portion and a second linear portion adjacent to each other in the plurality of linear portions sewn by the sewing apparatus are arranged to be separate on adjacent sheet members;
a thread member cutting apparatus to cut a thread member connecting portion of the thread member that lies between the first linear portion and the second linear portion; and
a cord member cutting apparatus to cut a cord connecting portion that connects the first linear portion and the second linear potion, at a predetermined position, wherein
the belt-like member is a belt-like absorbing member comprising an absorbing layer with liquid absorbability coated with a surface material of a thin film, and
the manufacturing system further comprises a belt-like member forming apparatus for covering the absorbing layer with the surface material.

9. A method for manufacturing a tampon comprising a sheet member and a cord member that is sewn onto a surface of the sheet member with a thread member and has an extended portion extending from an outer edge of the surface, the extended portion having a non-sewn area without the thread member, the method comprising:

forming a plurality of substantially U-shaped loosened portions for a cord member;

forming plural cut portions or openings for a belt-like member through which the plurality of loosened portions can be inserted;

inserting each of the plurality of loosened portions through each of the plural cut portions or each of the plural openings, and arranging a plurality linear portions of the cord member connecting the plurality of loosened portions with each other substantially linearly on a predetermined surface of the belt-like member;

sewing each of the plurality of linear portions of the cord member and belt-like member together using a thread member;

cutting a belt like member to form a plurality of sheet members in a prescribed shape so that a first linear portion and a second linear portion adjacent to each other in the plurality of linear portions sewn by sewing are arranged to be separate on adjacent sheet members;

cutting a thread member connecting portions of the thread member that lies between the first linear portion and the second linear portion; and cutting a cord connecting portions that connects the first linear portion and the second linear portion, at a predetermined position.

10. The method according to claim 9, wherein forming the plural cut portions or openings allow each of the plural out portions or openings to be formed at a substantially central position in a width direction of the belt-like member.

11. The method according to claim 9, wherein forming the plurality of loosened portions allows a predetermined portion of the cord member to be drawn to form each of the plurality of loosened portions, and inserting each of the plurality of loosened portions applies pressurized air to each of the plurality of loosened portions so as to insert each of the plurality of loosened portions into each of the plural cut portions or openings from the first surface to the second surface of the belt-lime member opposite to each other.

12. The method according to claim 9, where during arranging the plurality of linear portions of the cord member, the plurality of linear portions is allowed to substantially aligned in a line, and during sewing each of the plurality of linear portions of the cord member, each of the plurality of linear portions aligned is continuously sewn onto the belt-like member along a straight line formed by the plurality of linear portions.

13. A method for manufacturing a sheet-like structure comprising a sheet member and a cord member that is sewn onto a surface of the sheet member with a thread member and has an extended portion extending from an outer edge of the surface, the extended portion having a non-sewn without the thread member, the method comprising:

forming a plurality of substantially U-shaped loosened portions for a cord forming plural cut portions or openings for a belt-like member through which the plurality of loosened portions can be inserted;

inserting each of the plurality of loosened portions through each of the plural cut portions or each of the plural openings from a first surface to a second surface of the belt-like member opposite to each other, and arranging a plurality of linear portions of the cord members connecting the plurality of loosened portions with each other substantially linearly on a predetermined surface of the belt-like member;

sewing each of the plurality of linear portions of the cord member arranged and the belt-like member together using a thread member;

cutting the belt-like member to form a plurality of sheet members in a prescribed shape so that a first linear portion and a second linear portion adjacent to each other in the plurality of linear portions sewn by the sewing apparatus are arranged to be separate on adjacent sheet members;

cutting a thread member connecting portion of the thread member that lies between the first linear portion and the second linear portion; and cutting a cord connecting portion that connects the first linear portion and the second linear portion, at a predetermined position, wherein during arranging the plurality of linear portions of the cord member, the plurality of linear portions is allowed to be substantially aligned in a line, and during sewing each of the plurality of linear portions of the cord member, each of the plurality of linear portions aligned is continuously sewn onto the belt-like member along a straight line formed by the plurality of linear portions, and wherein sewing each of the plurality of linear portions of the cord member allowing each of the plurality of loosened portions to avoid overlapping the straight line formed by the plurality of linear portions.

14. A method for manufacturing a sheet-like structure comprising a sheet member and a cord member that is sewn onto a surface of the sheet member with a thread member and has an extended portion extending form an outer edge of the surface, the extended portion having a non-sewn area without the thread member, the method comprising:

forming a plurality of substantially U-shaped loosened portions for a cord member;

forming plural cut portions or openings for a belt-like member through which the plurality of loosened portions can be inserted;

inserting each of the plurality of loosened portions through each of the plural cut portions or each of the plural openings from a first surface to a second surface of the belt-like member opposite to each other, and arranging a plurality of linear portions of the cord member connecting the plurality of loosened portions with each other substantially linearly on a predetermined surface of the belt-like member;

sewing each of the plurality of linear portions of the cord member arranged and the belt-like member together using a thread member;

cutting the belt-like member to form a plurality of sheet members in a prescribed shape so that a first linear portion and a second linear portion adjacent to each other in the plurality of linear portions sewn by the sewing apparatus are arranged to be separate on adjacent sheet members;

cutting a thread member connecting portions of the thread member that lies between the first linear portion and the second linear portions; and cutting a cord connecting portion that connects the first linear portion and the second linear portion, at a predetermined position, wherein cutting the belt-like member comprises allowing the cord connecting portion to stay away from a cutting position at which the belt-like member is cut.

15. A method for manufacturing a sheet-like structure comprising a sheet member and a cord member that is sewn onto a surface of the sheet member with a thread member and has an extended portion extending from an outer edge of the surface, the extended portion having a non-sewn area without the thread member, the method comprising:

forming a plurality of substantially U-shaped loosened portions for a cord member;

forming plural cut portions or openings for a belt-like member through which the plurality of loosened portions can be inserted;

inserting each of the plurality of loosened portions through each of the plural cut portions or each of the plural openings from a first surface to a second surface of the belt-like member opposite to each other, and arranging a plurality of linear portions of the cord member connecting the plurality of loosened portions with each other substantially linearly on a predetermined surface of the belt-like member;

sewing each of the plurality of linear portions of the cord member arranged and the belt-like member together using a thread member;

cutting the belt-like member to form a plurality of sheet members in a prescribed shape so that a first linear portion and second linear portion adjacent to each other in the plurality of linear portions sewn by the sewing apparatus are arranged to be separate on adjacent sheet members;

cutting a thread member connecting portion of the thread member that lies between the first linear portion and the second linear portion; and cutting a cord connecting portion that connects the first linear portion and the second linear portion, at a predetermined position, wherein cutting the belt-like member, cutting the thread member and cutting the cord member step are performed by a cutting unit, and cutting the cord connecting portion comprises allowing the cord connecting portion to move to a cutting position provided in the cutting unit.

16. A method for manufacturing a sheet-like structure comprising a sheet member and a cord member that is sewn onto a surface of the sheet member with a thread member and has an extended portion extending from an outer edge of the surface, the extended portion having a non-sewn area without the thread member, the method comprising:

forming a plurality of substantially U-shaped loosened portions for a cord member;

forming plural cut portions or openings for a belt-like member through which the plurality of loosened portions can be inserted;

inserting each of the plurality of loosened portions through each of the plural cut portions or each of the plural openings from a first surface to a second surface of the belt-like member opposite to each other, and arranging a plurality of linear portions of the cord member connecting the plurality of loosened portions with each other substantially linearly on a predetermined surface of the belt-like member;

sewing each of the plurality of linear portions of the cord member arranged and the belt-like member to ether using a thread member;

cutting the belt-like member to form a plurality of sheet members in a prescribed shape so that a first linear portion and a second linear portion adjacent to each other in the plurality of linear portions sewn by the sewing apparatus are arranged to be separate on adjacent sheet members;

cutting a thread member connecting portion of the thread member that lies between the first linear portion and the second linear portion; and cutting a cord connecting portion that connects the first linear portion and the second linear portion, at a predetermined position, wherein the belt-like member is a belt-like absorbing member comprising an absorbing layer with liquid absorbability coated with a surface material of at thin film, and the method further comprises:

covering the absorbing layer with the surface material.

* * * * *